US008940298B2

(12) United States Patent
Wu et al.

(10) Patent No.: US 8,940,298 B2
(45) Date of Patent: Jan. 27, 2015

(54) HIGH AFFINITY ANTI-PROSTATE STEM CELL ANTIGEN (PSCA) ANTIBODIES FOR CANCER TARGETING AND DETECTION

(75) Inventors: Anna M. Wu, Sherman Oaks, CA (US); Robert E. Reiter, Los Angeles, CA (US); Eric J. Lepin, Los Angeles, CA (US); James D. Marks, Kensington, CA (US); Yu Zhou, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 543 days.

(21) Appl. No.: 12/676,348

(22) PCT Filed: Sep. 4, 2008

(86) PCT No.: PCT/US2008/075291
§ 371 (c)(1),
(2), (4) Date: Aug. 5, 2010

(87) PCT Pub. No.: WO2009/032949
PCT Pub. Date: Mar. 12, 2009

(65) Prior Publication Data
US 2010/0297004 A1     Nov. 25, 2010

Related U.S. Application Data

(60) Provisional application No. 60/969,939, filed on Sep. 4, 2007.

(51) Int. Cl.
*A61K 39/395* (2006.01)
*C07K 16/30* (2006.01)

(52) U.S. Cl.
CPC ....... *C07K 16/3069* (2013.01); *C07K 2317/622* (2013.01)
USPC .................. 424/130.1; 424/133.1; 424/138.1; 424/143.1; 424/155.1; 424/174.1; 435/7.1; 435/7.23; 536/23.5; 530/350; 530/387.1; 530/387.3; 530/387.7; 530/388.22; 530/388.8; 530/391.3; 530/391.7

(58) Field of Classification Search
USPC ........... 530/350, 387.1, 387.3, 387.7, 388.22, 530/388.8, 391.3, 391.7; 424/130.1, 133.1, 424/138.1, 143.1, 155.1, 174.1; 435/7.1, 435/7.23; 536/23.5
See application file for complete search history.

(56) References Cited

U.S. PATENT DOCUMENTS

| | | |
|---|---|---|
| 4,444,878 A | 4/1984 | Paulus |
| 4,892,824 A | 1/1990 | Skaletsky |
| 4,943,525 A | 7/1990 | Dawson |
| 5,256,395 A | 10/1993 | Barbet et al. |
| 5,292,668 A | 3/1994 | Paulus |
| 5,332,567 A | 7/1994 | Goldenberg |
| 5,376,249 A | 12/1994 | Afeyan et al. |
| 5,434,131 A | 7/1995 | Linsley |
| 5,436,170 A | 7/1995 | Cornell |
| 5,455,030 A | 10/1995 | Ladner et al. |
| 5,491,088 A | 2/1996 | Hellstrom |
| 5,518,889 A | 5/1996 | Ladner et al. |
| 5,523,210 A | 6/1996 | Paulus |
| 5,534,254 A | 7/1996 | Huston et al. |
| 5,559,099 A | 9/1996 | Wickham |
| 5,582,996 A | 12/1996 | Curtis |
| 5,591,828 A | 1/1997 | Bosslet et al. |
| 5,627,078 A | 5/1997 | Karl et al. |
| 5,637,481 A | 6/1997 | Ledbetter et al. |
| 5,660,827 A | 8/1997 | Thorpe |
| 5,688,690 A | 11/1997 | Valiante et al. |
| 5,693,477 A | 12/1997 | Cornell et al. |
| 5,705,614 A | 1/1998 | Ring |
| 5,712,136 A | 1/1998 | Wickham et al. |
| 5,731,168 A | 3/1998 | Carter |
| 5,731,190 A | 3/1998 | Wickham |
| 5,739,281 A | 4/1998 | Thogersen |
| 5,741,712 A | 4/1998 | Cornell |
| 5,747,035 A | 5/1998 | Presta et al. |
| 5,747,037 A | 5/1998 | Noelle |
| 5,762,930 A | 6/1998 | Fanger et al. |
| 5,766,960 A | 6/1998 | Cornell |
| 5,770,197 A | 6/1998 | Linsley |
| 5,773,253 A | 6/1998 | Linsley |
| 5,807,706 A | 9/1998 | Carter |
| 5,821,333 A | 10/1998 | Carter et al. |
| 5,830,473 A | 11/1998 | Thierfelder |
| 5,830,478 A | 11/1998 | Raso et al. |

(Continued)

FOREIGN PATENT DOCUMENTS

| | | |
|---|---|---|
| EP | 1005494 | 10/1998 |
| EP | 1780268 A2 | 12/1999 |

(Continued)

OTHER PUBLICATIONS

Bahrenberg et al. (Biochem. Biophys. Res. Commun. Sep. 7, 2000; 275 (3): 783-8).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*

(Continued)

*Primary Examiner* — Stephen Rawlings
(74) *Attorney, Agent, or Firm* — Morgan, Lewis & Bockius LLP; Annette S. Parent

(57) ABSTRACT

The present invention provides novel high affinity antibodies and fragments thereof that bind to the cancer antigen PSCA. The antibodies of the present invention may be used for cancer diagnosis, prognosis, treatment, visualization, and the like. The present invention also provides methods for the detection, visualization, and treatment of various cancers expressing PSCA.

33 Claims, 23 Drawing Sheets

(56) References Cited

U.S. PATENT DOCUMENTS

| | | |
|---|---|---|
| 5,837,242 A | 11/1998 | Holliger et al. |
| 5,837,281 A | 11/1998 | Iga et al. |
| 5,837,821 A | 11/1998 | Wu |
| 5,840,854 A | 11/1998 | Hellstrom et al. |
| 5,844,094 A | 12/1998 | Hudson et al. |
| 5,844,095 A | 12/1998 | Linsley |
| 5,846,782 A | 12/1998 | Wickham |
| 5,851,527 A | 12/1998 | Hansen |
| 5,851,795 A | 12/1998 | Linsley |
| 5,852,186 A | 12/1998 | Sodroski et al. |
| 5,855,866 A | 1/1999 | Thorpe |
| 5,861,156 A | 1/1999 | George et al. |
| 5,863,538 A | 1/1999 | Thorpe |
| 5,863,765 A | 1/1999 | Berry et al. |
| 5,869,045 A | 2/1999 | Hellstrom |
| 5,869,049 A | 2/1999 | Noelle et al. |
| 5,869,620 A | 2/1999 | Whitlow et al. |
| 5,872,222 A | 2/1999 | Chang |
| 5,876,691 A | 3/1999 | Chester et al. |
| 5,876,718 A | 3/1999 | Noelle |
| 5,877,289 A | 3/1999 | Thorpe |
| 5,877,291 A | 3/1999 | Mezes et al. |
| 5,885,579 A | 3/1999 | Linsley |
| 5,885,796 A | 3/1999 | Linsley |
| 5,892,020 A | 4/1999 | Mezes |
| 5,917,018 A | 6/1999 | Thogersen |
| 5,932,448 A | 8/1999 | Tso et al. |
| 5,942,229 A | 8/1999 | Noelle et al. |
| 5,951,982 A | 9/1999 | Zoller et al. |
| 5,959,083 A | 9/1999 | Bosslet et al. |
| 5,962,311 A | 10/1999 | Wickham |
| 5,965,132 A | 10/1999 | Thorpe |
| 5,965,541 A | 10/1999 | Wickham |
| 5,968,510 A | 10/1999 | Linsley |
| 5,977,318 A | 11/1999 | Linsley |
| 5,980,896 A | 11/1999 | Hellstrom et al. |
| 5,989,830 A | 11/1999 | Davis et al. |
| 5,990,275 A | 11/1999 | Whitlow et al. |
| 5,994,519 A | 11/1999 | Osbourn |
| 6,004,554 A | 12/1999 | Thorpe |
| 6,004,555 A | 12/1999 | Thorpe |
| 6,010,884 A | 1/2000 | Griffiths |
| 6,010,902 A | 1/2000 | Ledbetter et al. |
| 6,020,145 A | 2/2000 | Hellstrom |
| 6,030,792 A | 2/2000 | Otterness et al. |
| 6,051,230 A | 4/2000 | Thorpe |
| 6,057,155 A | 5/2000 | Wickham |
| 6,071,490 A | 6/2000 | Griffiths et al. |
| 6,083,477 A | 7/2000 | Goldenberg |
| 6,083,763 A | 7/2000 | Balch |
| 6,090,914 A | 7/2000 | Linsley |
| 6,093,399 A | 7/2000 | Thorpe |
| 6,096,289 A | 8/2000 | Goldenberg |
| 6,096,871 A | 8/2000 | Presta et al. |
| 6,099,841 A | 8/2000 | Hillan et al. |
| 6,106,835 A | 8/2000 | Chang |
| 6,117,982 A | 9/2000 | Chang |
| 6,121,022 A | 9/2000 | Presta et al. |
| 6,129,916 A | 10/2000 | Chang |
| 6,132,992 A | 10/2000 | Ledbetter |
| 6,150,508 A | 11/2000 | Murphy et al. |
| 6,180,336 B1 | 1/2001 | Osbourn |
| 6,187,284 B1 | 2/2001 | Griffiths |
| 6,193,966 B1 | 2/2001 | Deo et al. |
| 6,193,967 B1 | 2/2001 | Morganelli |
| 6,197,298 B1 | 3/2001 | Chang |
| 6,200,765 B1 | 3/2001 | Murphy et al. |
| 6,201,167 B1 | 3/2001 | Pothier |
| 6,241,961 B1 | 6/2001 | Benes et al. |
| 6,248,516 B1 | 6/2001 | Winter et al. |
| 6,258,939 B1 | 7/2001 | Reiter et al. |
| 6,261,535 B1 | 7/2001 | Thorpe |
| 6,261,789 B1 | 7/2001 | Reiter et al. |
| 6,261,791 B1 | 7/2001 | Reiter |
| 6,267,960 B1 | 7/2001 | Reiter et al. |
| 6,284,742 B1 | 9/2001 | Curiel et al. |
| 6,290,955 B1 | 9/2001 | Thierfelder |
| 6,294,391 B1 | 9/2001 | Badley et al. |
| 6,312,692 B1 | 11/2001 | Noelle |
| 6,312,694 B1 | 11/2001 | Thorpe et al. |
| 6,312,960 B1 | 11/2001 | Balch |
| 6,319,500 B1 | 11/2001 | Goldenberg |
| 6,329,190 B1 | 12/2001 | Wickham |
| 6,331,441 B1 | 12/2001 | Balch |
| 6,342,219 B1 | 1/2002 | Thorpe |
| 6,342,221 B1 | 1/2002 | Thorpe |
| 6,342,587 B1 | 1/2002 | Barbas, III et al. |
| 6,342,588 B1 | 1/2002 | Osbourn |
| 6,346,249 B1 | 2/2002 | Barbos, III |
| 6,358,489 B1 | 3/2002 | Griffiths |
| 6,361,774 B1 | 3/2002 | Griffiths et al. |
| 6,368,596 B1 | 4/2002 | Ghetie et al. |
| 6,383,759 B1 | 5/2002 | Murphy et al. |
| 6,387,350 B2 | 5/2002 | Goldenberg |
| 6,395,276 B1 | 5/2002 | Rybak |
| 6,399,068 B1 | 6/2002 | Goldenberg |
| 6,416,758 B1 | 7/2002 | Thorpe |
| 6,451,312 B1 | 9/2002 | Thorpe |
| 6,458,933 B1 | 10/2002 | Hansen |
| 6,465,253 B1 | 10/2002 | Wickham |
| 6,479,301 B1 | 11/2002 | Balch |
| 6,482,919 B2 | 11/2002 | Ledbetter |
| 6,489,123 B2 | 12/2002 | Osbourn |
| 6,492,123 B1 | 12/2002 | Holliger |
| 6,524,583 B1 | 2/2003 | Thorpe |
| 6,541,212 B2 | 4/2003 | Reiter et al. |
| 6,545,142 B1 | 4/2003 | Winter |
| 6,548,275 B2 | 4/2003 | Goldenberg |
| 6,573,096 B1 | 6/2003 | Chen |
| 6,589,527 B1 | 7/2003 | Winter |
| 6,602,684 B1 | 8/2003 | Umana et al. |
| 6,623,940 B1 | 9/2003 | Ledbetter |
| 6,642,007 B1 | 11/2003 | Saltarelli |
| 6,649,163 B1 | 11/2003 | Bander |
| 6,649,407 B2 | 11/2003 | Wickham |
| 6,653,104 B2 | 11/2003 | Goldenberg |
| 6,676,941 B2 | 1/2004 | Thorpe |
| 6,703,020 B1 | 3/2004 | Thorpe |
| 6,709,844 B1 | 3/2004 | Levy |
| 6,749,853 B1 | 6/2004 | Thorpe |
| 6,756,036 B2 | 6/2004 | Reiter |
| 6,790,939 B2 | 9/2004 | Reiter |
| 6,803,238 B1 | 10/2004 | Eggers |
| 6,824,780 B1 | 11/2004 | Devaux et al. |
| 6,825,326 B2 | 11/2004 | Reiter |
| 6,835,866 B1 | 12/2004 | Mangelsdorf et al. |
| 6,861,234 B1 | 3/2005 | Simard et al. |
| 6,869,620 B2 | 3/2005 | Moore |
| 6,870,034 B2 | 3/2005 | Breece et al. |
| 6,881,822 B2 | 4/2005 | Reiter |
| 6,887,468 B1 | 5/2005 | Thorpe |
| 6,887,471 B1 | 5/2005 | Linsley |
| 6,887,975 B2 | 5/2005 | Afar et al. |
| 6,951,755 B2 | 10/2005 | Wickham |
| 6,953,567 B2 | 10/2005 | Griffiths |
| 6,960,443 B2 | 11/2005 | Reiter |
| 6,962,981 B1 | 11/2005 | Murphy |
| 6,977,074 B2 | 12/2005 | Kundig et al. |
| 6,979,730 B2 | 12/2005 | Reiter |
| 6,994,851 B1 | 2/2006 | Kundig et al. |
| 6,998,253 B1 | 2/2006 | Presta |
| 7,033,572 B2 | 4/2006 | Goldenberg |
| 7,033,798 B2 | 4/2006 | Plückthun et al. |
| 7,053,186 B2 | 5/2006 | Afar et al. |
| 7,056,509 B2 | 6/2006 | Thorpe |
| 7,105,166 B1 | 9/2006 | Linsley |
| 7,112,317 B2 | 9/2006 | Thorpe |
| 7,122,646 B2 | 10/2006 | Holliger et al. |
| 7,125,541 B2 | 10/2006 | Thorpe |
| 7,159,826 B1 | 1/2007 | Bruce |
| 7,201,890 B2 | 4/2007 | Goldenberg |
| 7,201,900 B2 | 4/2007 | Murphy et al. |
| 7,230,084 B2 | 6/2007 | Hansen |
| 7,232,682 B2 | 6/2007 | Simard et al. |

(56) References Cited

U.S. PATENT DOCUMENTS

| | | |
|---|---|---|
| 7,235,641 B2 | 6/2007 | Kufer et al. |
| 7,250,492 B2 | 7/2007 | Chen |
| 7,306,907 B2 | 12/2007 | Winter |
| 7,311,910 B2 | 12/2007 | Linsley |
| 7,323,553 B2 | 1/2008 | Fahrner et al. |
| 7,364,729 B2 | 4/2008 | Kundig et al. |
| 7,375,078 B2 | 5/2008 | Feng |
| 7,381,407 B1 | 6/2008 | Murphy |
| 7,390,654 B2 | 6/2008 | Levy |
| 7,407,656 B2 | 8/2008 | Reiter |
| 7,413,852 B2 | 8/2008 | Balch |
| 7,417,113 B2 | 8/2008 | Reiter |
| 7,435,416 B2 | 10/2008 | Devaux et al. |
| 7,452,539 B2 | 11/2008 | Emery et al. |
| 7,462,691 B2 | 12/2008 | Reiter |
| 7,470,429 B2 | 12/2008 | Griffiths |
| 7,476,385 B2 | 1/2009 | Noelle |
| 7,476,513 B2 | 1/2009 | Murphy |
| 7,485,296 B2 | 2/2009 | Reiter |
| 7,485,704 B2 | 2/2009 | Fahrner et al. |
| 7,494,646 B2 | 2/2009 | Jakobovits et al. |
| 7,498,298 B2 | 3/2009 | Doronina et al. |
| 7,517,670 B2 | 4/2009 | Umana et al. |
| 7,521,541 B2 | 4/2009 | Eigenbrot et al. |
| 7,524,813 B2 | 4/2009 | Zundel et al. |
| 7,527,786 B2 | 5/2009 | Reiter |
| 7,541,442 B2 | 6/2009 | Gudas et al. |
| 7,572,772 B2 | 8/2009 | Linsley |
| 7,595,379 B2 | 9/2009 | Gudas et al. |
| 7,612,181 B2 | 11/2009 | Wu et al. |
| 7,622,564 B2 | 11/2009 | Ge et al. |
| 7,622,569 B2 | 11/2009 | Raitano et al. |
| 7,642,228 B2 | 1/2010 | Carter et al. |
| 7,662,936 B2 | 2/2010 | Kadkhodayan et al. |
| 7,691,380 B2 | 4/2010 | Thorpe |
| 7,695,936 B2 | 4/2010 | Carter et al. |
| 7,722,874 B2 | 5/2010 | Noelle et al. |
| 7,745,394 B2 | 6/2010 | Doronina et al. |
| 7,754,681 B2 | 7/2010 | Feng |
| 7,807,799 B2 | 10/2010 | Fahrner et al. |
| 7,820,166 B2 | 10/2010 | Lanzavecchia |
| 7,838,637 B2 | 11/2010 | Kontermann |
| 7,855,275 B2 | 12/2010 | Eigenbrot et al. |
| 7,867,483 B2 | 1/2011 | Delcayre et al. |
| 7,884,179 B2 | 2/2011 | Faris et al. |
| 7,888,035 B2 | 2/2011 | Klass et al. |
| 7,897,356 B2 | 3/2011 | Klass et al. |
| 7,906,329 B2 | 3/2011 | Umana et al. |
| 7,915,395 B2 | 3/2011 | Ledbetter |
| 7,939,503 B2 | 5/2011 | Jakobovits et al. |
| 7,947,276 B2 | 5/2011 | Jakobovits et al. |
| 7,947,839 B2 | 5/2011 | Gazzard et al. |
| 7,960,109 B2 | 6/2011 | Hessels et al. |
| 7,964,566 B2 | 6/2011 | Doronina et al. |
| 7,964,567 B2 | 6/2011 | Doronina et al. |
| 7,989,434 B2 | 8/2011 | Feng |
| 7,994,135 B2 | 8/2011 | Doronina et al. |
| 7,998,701 B2 | 8/2011 | Chua et al. |
| 8,007,994 B2 | 8/2011 | Mangelsdorf et al. |
| 8,008,442 B2 | 8/2011 | Jakobovits et al. |
| 8,012,937 B2 | 9/2011 | Raitano et al. |
| 8,013,128 B2 | 9/2011 | Gudas et al. |
| 8,013,135 B2 | 9/2011 | Jakobovits et al. |
| 8,088,908 B2 * | 1/2012 | Sherman et al. ............ 536/23.53 |
| 8,206,932 B2 | 6/2012 | Gudas et al. |
| 8,278,424 B2 | 10/2012 | Gudas et al. |
| 8,309,300 B2 | 11/2012 | Junutula et al. |
| 2001/0006618 A1 | 7/2001 | Goldenberg |
| 2001/0055595 A1 | 12/2001 | Goldenberg |
| 2001/0055751 A1 | 12/2001 | Saffran |
| 2002/0004215 A1 | 1/2002 | Osbourn et al. |
| 2002/0012989 A1 | 1/2002 | Ledbetter |
| 2002/0037289 A1 | 3/2002 | Thorpe et al. |
| 2002/0102666 A1 | 8/2002 | Reiter |
| 2002/0114808 A1 | 8/2002 | Griffiths |
| 2002/0119096 A1 | 8/2002 | Griffiths |
| 2002/0119153 A1 | 8/2002 | Thorpe et al. |
| 2002/0119157 A1 | 8/2002 | Reiter |
| 2002/0132979 A1 | 9/2002 | Chen |
| 2002/0136689 A1 | 9/2002 | Reiter et al. |
| 2002/0136690 A1 | 9/2002 | Goldenberg |
| 2002/0141941 A1 | 10/2002 | Reiter |
| 2002/0146369 A1 | 10/2002 | Goldenberg |
| 2002/0151027 A1 | 10/2002 | Wickham |
| 2002/0155537 A1 | 10/2002 | Carter |
| 2002/0187135 A1 | 12/2002 | Noelle |
| 2002/0187153 A1 | 12/2002 | Goldenberg |
| 2002/0192223 A1 | 12/2002 | Hellstrom |
| 2003/0022355 A1 | 1/2003 | Wickham |
| 2003/0031669 A1 | 2/2003 | Goldenberg |
| 2003/0068322 A1 | 4/2003 | Hansen |
| 2003/0103982 A1 | 6/2003 | Hansen |
| 2003/0113818 A1 | 6/2003 | Reiter |
| 2003/0113820 A1 | 6/2003 | Reiter |
| 2003/0114368 A1 | 6/2003 | Rybak |
| 2003/0114659 A1 | 6/2003 | Winter |
| 2003/0118583 A1 | 6/2003 | Emery et al. |
| 2003/0130496 A1 | 7/2003 | Winter |
| 2003/0147806 A1 | 8/2003 | Reiter |
| 2003/0153016 A1 | 8/2003 | Reiter |
| 2003/0170228 A1 | 9/2003 | Ashkenazi et al. |
| 2003/0170697 A1 | 9/2003 | Goldenberg |
| 2003/0175900 A1 | 9/2003 | Ashkenazi et al. |
| 2003/0185832 A1 | 10/2003 | Thorpe |
| 2003/0211096 A1 | 11/2003 | Ashkenazi et al. |
| 2003/0219441 A1 | 11/2003 | Thorpe |
| 2003/0219876 A1 | 11/2003 | Ledbetter |
| 2003/0228318 A1 | 12/2003 | Reiter |
| 2004/0018519 A1 | 1/2004 | Wright, Jr. |
| 2004/0018571 A1 | 1/2004 | Reiter |
| 2004/0023249 A1 | 2/2004 | Balch |
| 2004/0024188 A1 | 2/2004 | Murphy |
| 2004/0038339 A1 | 2/2004 | Kufer et al. |
| 2004/0043029 A1 | 3/2004 | Hellstrom |
| 2004/0058400 A1 | 3/2004 | Holliger |
| 2004/0110941 A2 | 6/2004 | Winter |
| 2004/0115202 A1 | 6/2004 | Chen |
| 2004/0162411 A1 | 8/2004 | Lanzavecchia |
| 2004/0241817 A1 | 12/2004 | Umana et al. |
| 2005/0003465 A1 | 1/2005 | Reiter |
| 2005/0026178 A1 | 2/2005 | Nilsen-Hamilton |
| 2005/0026229 A1 | 2/2005 | Reiter |
| 2005/0036942 A1 | 2/2005 | Devaux et al. |
| 2005/0059099 A1 | 3/2005 | Reiter |
| 2005/0069543 A1 | 3/2005 | Thierfelder |
| 2005/0136050 A1 | 6/2005 | Kufer et al. |
| 2005/0152909 A1 | 7/2005 | Reiter |
| 2005/0163780 A1 | 7/2005 | Noelle |
| 2005/0169919 A1 | 8/2005 | Linsley |
| 2005/0169930 A1 | 8/2005 | Reiter |
| 2005/0175582 A1 | 8/2005 | Goldenberg |
| 2005/0215769 A1 | 9/2005 | Breece et al. |
| 2005/0232929 A1 | 10/2005 | Kadkhodayan et al. |
| 2005/0239116 A1 | 10/2005 | Willey |
| 2005/0249738 A1 | 11/2005 | Goldenberg |
| 2005/0272128 A1 | 12/2005 | Umana et al. |
| 2005/0277193 A1 | 12/2005 | Wickham |
| 2006/0018914 A1 | 1/2006 | Hellstrom |
| 2006/0147375 A1 | 7/2006 | Gudas et al. |
| 2006/0159689 A1 | 7/2006 | Chiang et al. |
| 2006/0210473 A1 | 9/2006 | Thorpe |
| 2006/0222649 A1 | 10/2006 | Noelle |
| 2006/0234226 A1 | 10/2006 | Fahner et al. |
| 2006/0234271 A1 | 10/2006 | Su |
| 2006/0246524 A1 | 11/2006 | Bauer et al. |
| 2006/0269540 A1 | 11/2006 | Robert et al. |
| 2006/0269557 A1 | 11/2006 | Sherman et al. |
| 2006/0275312 A1 | 12/2006 | Chua et al. |
| 2007/0014794 A1 | 1/2007 | Carter |
| 2007/0031922 A1 | 2/2007 | Presta |
| 2007/0059306 A1 | 3/2007 | Grosmaire |
| 2007/0128671 A1 | 6/2007 | Murphy |
| 2007/0134243 A1 | 6/2007 | Gazzard et al. |
| 2007/0207146 A1 | 9/2007 | Hansen |

(56) References Cited

U.S. PATENT DOCUMENTS

| | | |
|---|---|---|
| 2007/0212331 A1 | 9/2007 | Baldassare et al. |
| 2007/0243950 A1 | 10/2007 | Billings |
| 2007/0253950 A1 | 11/2007 | Jacobsen |
| 2007/0286858 A1 | 12/2007 | Clancy |
| 2008/0031876 A1 | 2/2008 | Linsley |
| 2008/0166759 A1 | 7/2008 | Presta |
| 2008/0171040 A1 | 7/2008 | Ebens et al. |
| 2008/0206192 A1 | 8/2008 | Moller et al. |
| 2008/0213256 A1 | 9/2008 | Kufer et al. |
| 2008/0213921 A1 | 9/2008 | Robertson et al. |
| 2008/0227736 A1 | 9/2008 | Chen et al. |
| 2008/0267872 A1 | 10/2008 | Raitano et al. |
| 2008/0299618 A1 | 12/2008 | Winter |
| 2008/0305105 A1 | 12/2008 | Kufer et al. |
| 2008/0305476 A1 | 12/2008 | Robertson et al. |
| 2008/0318253 A9 | 12/2008 | Reiter |
| 2008/0318254 A9 | 12/2008 | Reiter |
| 2009/0004109 A1 | 1/2009 | Jacobovits et al. |
| 2009/0022738 A1 | 1/2009 | Hofmeister et al. |
| 2009/0041758 A1 | 2/2009 | Glaser |
| 2009/0041791 A1 | 2/2009 | Feng |
| 2009/0053223 A1 | 2/2009 | Hoffmann et al. |
| 2009/0099344 A1 | 4/2009 | Fahrner et al. |
| 2009/0104631 A1 | 4/2009 | Reiter |
| 2009/0136475 A1 | 5/2009 | Barth |
| 2009/0169613 A1 | 7/2009 | Reznik et al. |
| 2009/0202548 A1 | 8/2009 | Gudas et al. |
| 2009/0214539 A1 | 8/2009 | Grosmaire |
| 2009/0226465 A1 | 9/2009 | Jackson |
| 2009/0238755 A1 | 9/2009 | Bander |
| 2009/0239759 A1 | 9/2009 | Balch |
| 2009/0272169 A1 | 11/2009 | Pan |
| 2009/0275081 A1 | 11/2009 | Barat et al. |
| 2009/0286258 A1 | 11/2009 | Kaur et al. |
| 2009/0311181 A1* | 12/2009 | Wu et al. .................. 424/9.1 |
| 2009/0317397 A1 | 12/2009 | Linsley |
| 2010/0003766 A1 | 1/2010 | Eigenbrot et al. |
| 2010/0034837 A1 | 2/2010 | Beria et al. |
| 2010/0047239 A1 | 2/2010 | Wu et al. |
| 2010/0055120 A1 | 3/2010 | Ge et al. |
| 2010/0058803 A1 | 3/2010 | Ransbarger |
| 2010/0069616 A1 | 3/2010 | Wu et al. |
| 2010/0111856 A1 | 5/2010 | Gill et al. |
| 2010/0135900 A1 | 6/2010 | Cerveny |
| 2010/0184046 A1 | 7/2010 | Klass et al. |
| 2010/0189651 A1 | 7/2010 | Stagliano |
| 2010/0215581 A1 | 8/2010 | Hoffmann |
| 2010/0254986 A1 | 10/2010 | Carter |
| 2010/0255479 A1 | 10/2010 | Mikolajczyk et al. |
| 2010/0266491 A1 | 10/2010 | Farokhzad et al. |
| 2010/0267933 A1 | 10/2010 | Wilson |
| 2010/0278919 A1 | 11/2010 | Denes et al. |
| 2010/0297004 A1 | 11/2010 | Wu et al. |
| 2010/0303821 A1 | 12/2010 | Ashman |
| 2011/0006466 A1 | 1/2011 | Ichikawa |
| 2011/0009001 A1 | 1/2011 | Chen |
| 2011/0020327 A1 | 1/2011 | Moya et al. |
| 2011/0076287 A1 | 3/2011 | Cohen et al. |
| 2011/0081345 A1 | 4/2011 | Moore |
| 2011/0086050 A1 | 4/2011 | Presta |
| 2011/0104059 A1 | 5/2011 | St. Croix et al. |
| 2011/0110852 A1 | 5/2011 | Miller et al. |
| 2011/0117023 A1 | 5/2011 | Yamauchi |
| 2011/0123532 A1 | 5/2011 | Gurney et al. |
| 2011/0137017 A1 | 6/2011 | Eigenbrot et al. |
| 2011/0142811 A1 | 6/2011 | Ungerechts |
| 2011/0207155 A1 | 8/2011 | Pengo et al. |
| 2011/0262968 A1 | 10/2011 | Gudas et al. |
| 2011/0268656 A1 | 11/2011 | Ho |
| 2012/0077962 A1* | 3/2012 | Sherman et al. .......... 530/387.3 |

FOREIGN PATENT DOCUMENTS

| | | |
|---|---|---|
| EP | 1550729 | 7/2005 |
| EP | 1997514 | 12/2008 |
| EP | 1629011 B1 | 1/2010 |
| EP | 2226394 A1 | 9/2010 |
| EP | 2260858 A2 | 12/2010 |
| JP | 2003-504414 | 2/2003 |
| WO | WO 93/15199 | 8/1993 |
| WO | WO 94/09820 | 5/1994 |
| WO | WO 96/08570 | 3/1996 |
| WO | WO 96/26272 | 8/1996 |
| WO | WO 97/35616 | 10/1997 |
| WO | WO 99/56779 | 11/1999 |
| WO | WO 00/14234 | 3/2000 |
| WO | WO 01/05427 | 1/2001 |
| WO | WO 01/05427 A1 | 1/2001 |
| WO | WO 01/09303 | 2/2001 |
| WO | WO 01/40309 | 6/2001 |
| WO | WO 01/82963 | 11/2001 |
| WO | WO 02/22680 | 3/2002 |
| WO | WO 03/008537 | 1/2003 |
| WO | WO 03/050140 | 6/2003 |
| WO | WO 2004/106380 | 12/2004 |
| WO | WO 2005/000899 A2 | 1/2005 |
| WO | WO 2005/000899 A3 | 1/2005 |
| WO | WO 2005/026334 | 3/2005 |
| WO | WO 2005/043165 | 5/2005 |
| WO | WO 2005/061547 | 7/2005 |
| WO | WO 2005/068616 | 7/2005 |
| WO | WO 2006/112933 | 10/2006 |
| WO | WO 2007/001476 | 1/2007 |
| WO | WO 2007/064345 | 6/2007 |
| WO | WO 2007/100385 | 9/2007 |
| WO | WO 2007/109321 | 9/2007 |
| WO | WO 2007/137117 | 11/2007 |
| WO | WO 2009/003492 | 7/2008 |
| WO | WO 2009/032949 | 3/2009 |
| WO | WO 2009/039854 | 4/2009 |
| WO | WO 2009/052328 | 4/2009 |
| WO | WO 2010/037835 | 4/2009 |
| WO | WO 2009/076099 | 6/2009 |
| WO | WO 2009/082443 | 7/2009 |
| WO | WO 2010/037395 | 4/2010 |
| WO | WO 2010/037397 | 4/2010 |
| WO | WO 2010/037539 | 4/2010 |
| WO | WO 2010/102195 | 9/2010 |
| WO | WO 2011/000054 | 1/2011 |
| WO | WO 2011/056983 | 5/2011 |
| WO | WO 2011/069019 | 6/2011 |
| WO | WO 2011/075786 | 6/2011 |
| WO | WO 2011/090762 | 7/2011 |
| WO | WO 2011/109440 | 9/2011 |

OTHER PUBLICATIONS

Caldas et al. (Mol. Immunol. May 2003; 39 (15): 941-952).*
Winkler et al. (J. Immunol. Oct. 15, 2000; 165 (8): 4505-4514).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Stancoviski et al. (Proceedings of the National Academy of Science USA. 1991; 88: 8691-8695).*
Jiang et al. (J. Biol. Chem. Feb. 11, 2005; 280 (6): 4656-4662).*
Campbell et al (Blood Reviews. 2003; 17:143-152).*
Henry et al. (Cancer Res. Nov. 1, 2004; 64: 7995-8001).*
McDevitt et al. (Cancer Res. Nov. 1, 2000; 60: 6095-6100).*
Pettersen et al. (J. Immunol. Jun. 15, 1999; 162 (12): 7031-7040).*
Bernard et al. (Human Immunol. 1986; 17: 388-405).*
Kipps et al. (J. Exp. Med. Jan. 1, 1985; 161 (1): 1-17).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*

(56) References Cited

OTHER PUBLICATIONS

Bergers et al. (Current Opinion in Genetics and Development. 2000; 10: 120-127).*
Olafsen et al. (J. Immunother. May-Jun. 2007; 30 (4): 396-405).*
Williams et al. (Cancer Biother. Radiopharm. Feb. 2001; 16 (1): 25-35).*
Gu et al. (Cancer Res. 2005; 65 (20): 9495-500).*
Saffran et al. (Proc. Natl. Acad. Sci. USA. 2001; 98 (5): 2658-63).*
Yazaki et al. (Protein Eng. Des. Sei. 2004; 17 (5): 481-9).*
Gu et al. (Oncogene. 2000; 19: 1288-96).*
Hu et al. (Cancer Res. 1996; 56 (13): 3055-61).*
Yazaki et al. (Bioconjug. Chem. 2001; 12 (2): 220-8).*
Adams et al., "Prolonged in vivo tumour retention of a human diabody targeting the extracellular domain of human HER2/neu", British Journal of Cancer (1998) 77(9), 1405-1412.
Albrecht, H. et al., "Production of Soluble ScFvs with C-Temninal-Free Thiol for Site-Specific Conjugation or Stable Dimeric ScFvs on Demand," Bioconjugate Chemistry, 2004, vol. 15, No. 1, pp. 16-26.
Ballou, B. et al., "Noninvasive Imaging of Quantum Dots in Mice," Bioconjugate Chem., 2004, vol. 15, pp. 79-86.
Bruchez, Jr., M. et al., "Semiconductor Nanocrystals as Fluorescent Biological Labels," Science, Sep. 25, 1998, vol. 281, pp. 2013-2016.
Carmichael, Ja et al., "The Crystal Structure of an Ani-CEA scFV Diabody Assembled from T84.66 scFvs in VL-to-VH Orientation: Implications for Diabody Flexibility," J. Mol. Biol., 2003, vol. 326, pp. 341-351.
Chan, W.C. et al., "Quantum Dot Bioconjugates for Ultrasensitive Nonisotopic Detection," Science, Sep. 25, 1998, vol. 281, pp. 2016-2018.
Fountaine, T.J. et al., "Multispectral imaging of clinically relevant cellular targets in tonsil and lymphoid tissue using semiconductor quantum dots," Modern Pathology, 2006, vol. 19, pp. 1181-1191.
Galfre, G. et al., "Preparation of Monoclonal Antibodies: Strategies and Procedures," Methods in Enzymology, 1981, vol. 73, pp. 3-46.
Gao, X. et al., "In vivo cancer targeting and imaging with semiconductor quantum dots," Nature Biotechnology, Aug. 2004, vol. 22, No. 8, pp. 969-976.
Gu, Z. et al., "Prostate stem cell antigen (PSCA) expression increases with high gleason score, advanced stage and bone metastasis in prostate cancer," Oncogene, 2000, vol. 19, pp. 1288-1296.
Gu, Z. "Biological activity and microPET imaging properties of chimeric and humanized anti-prostate stem cell antigen (PSCA) antibodies" Biological Abstracts, vol. 46, Abstract No. 696 (2005).
Holliger, P. et al., "'Diabodies': Small bivalent and bispecific antibody fragments," Proc. Natl. Acad. Sci. USA, Jul. 1993, vol. 90, pp. 6444-6448.
Hollinger et al., "Engineered Antibody Fragments and the Rise of Single Domains", Nature Biotechnology (Nature Publishing Group, NY, NY, USA), vol. 23, No. 9 (2005) pp. 1126-1136.
Howarth, M. et al., "Targeting quantum dots to surface proteins in living cells with biotin ligase," PNAS, May 24, 2005, vol. 102, No. 21, pp. 7583-7588.
Hu, S-Z. et al., "Minibody: A Novel Engineered Anti-Carcinoembryonic Antigen Antibody Fragment (Single-Chain Fv-CH3) Which Exhibits Rapid, High-Level Targeting of Xenografts," Cancer Research, (1996).
Jaiswal, J.K. et al., "Long-term multiple color imaging of live cells using quantum dot bioconjugates," Nature Biotechnology, Jan. 2003, vol. 21, pp. 47-51.
Jaiswal, J.K. et al., "Use of quantum dots for live cell imaging," Nature Methods, Oct. 2004, vol. 1, No. 1, pp. 73-78.
Kenanova, V. et al., "Tailoring antibodies for radionudide delivery," Expert Opin. Drug Deliv., 2006, vol. 3, No. 1, pp. 53-70.
Kim, S. et al., "Near-infrared fluorescent type II quantum dots for sentinel lymph node mapping," Nature Biotechnology, Jan. 2004, vol. 22, No. 1, pp. 93-97.
Leyton et al. "Anti-Prostate Sem Cell antigen (PSCA) Antibody Fragments for PET Imaging of Prostate Cancer," Cancer Biotherapy & Radiopharmaceuticals (Mary Ann Liebert, USA), vol. 21, No. 4 (2006) p. 391.

Li, L. et al., "Reduction of Kidney Uptake in Radiometal Labeled Peptide Linkers Conjugated to Recombinant Antibody Fragments. Site Specific Conjugation of DOTA-Peptides to a Cys-Diabody," Bioconjugate Chem., 2002, vol. 13, No. 5, pp. 985-995.
Maysinger, D. et al., "Real-Time Imaging of Astrocyte Response to Quantum Dots: In Vivo Screening Model System for Biocompatibility of Nanoparticles," Nano Letters, 2007, vol. 7, No. 8, pp. 2513-2520.
Medintz, I.L. et al., "Self-assembled nanoscale biosensors based on quantum dot FRET donors," Nature Materials, Sep. 2003, vol. 2, pp. 630-638.
Michalet, X. et al., "Quantum Dots for Live Cells, in Vivo Imaging, and Diagnostics," Science, Jan. 28, 2005, vol. 307, pp. 538-544.
Olafsen, T. et al., "Covalent disulfide-linked anti-CEA diabody allows site-specific conjugation and radiolabeling for tumor targeting applications," Protein Engineering, Design & Selection, 2004, vol. 17, No. 1, pp. 21-27.
Olafsen et al. "Targeting, imaging, and therapy using a humanized antiprostate stem cell antigen (PSCA) antibody," Journal of Immunotherapy (Lippincott Williams & Wilkins, Hagerstown, MD., USA), vol. 30 No. 4 (2007) pp. 396-405.
Olafsen, T. et al., "Optimizing Radiolabeled Engineered Anti_ p185HER2 Antibody Fragments for in vivo Imaging," Cancer Research, Jul. 1, 2005, vol. 65, No. 13, pp. 5907-5916.
Saffran et al., "Anti-PSCA MABS Inhibit Tumor Growth and Metastasis Formation and Prolong the Survival of Mice Bearing Human Prostate Cancer Xenografts," Proceedings of the National Academy of Sciences of the United States (PNAS), National Academy of Science, US, vol. 98, No. 5 (2001) pp. 2658-2663.
Smith, B.R. et al., "Real-Time Intravital Imaging of RGD-Quantum Dot Binding to Luminal Endothelium in Mouse Tumor Neovasculature," Nano Letters, Sep. 2008, vol. 8, No. 9, pp. 2599-2606.
So, M-K. et al., "Self-illuminating quantum dot conjugates for in vivo imaging," Nature Biotechnology, Mar. 2006, vol. 24, No. 3, pp. 339-343.
Stroh, M. et al., "Quantum dots spectrally distinguish multiple species within the tumor milieu in vivo," Nature Medicine, Jun. 2005, vol. 11, No. 6, pp. 678-682.
Sundaresan, G. et al., "$^{124}$I-Labeled Engineered Anti-CEA Minibodies and Diabodies Allow High-Contrast, Antigen-Specific Small-Animal PET Imaging of Xenografts in Athymic Mice," The Journal of Nuclear Medicine, Dec. 2003, vol. 44, No. 12, pp. 1962-1969.
Tada, H. et al., "In vivo Real-time Tracking of Single Quantum Dots Conjugated with 29. Monoclonal Anti-HER2 Antibody in Tumors of Mice," Cancer Research, Feb. 1, 2007, vol. 67, No. 3, pp. 1138-1144.
Voura, E.B. et al., "Tracking metastatic tumor cell extravasation with quantum dot 30. nanocrystals and fluorescence emission-scanning microscopy," Nature Medicine, Sep. 2004, vol. 10, No. 9, pp. 993-998.
Wu, A.M. et al., "High-Resolution MicroPET Imaging of Carcinoembryonic Antigen-Positive Xenografts by Using a Copper-64-Labeled Engineered Antibody Fragment," PNAS, (2000), vol. 97, No. 15, pp. 8495-8500.
Wu, A.M. et al., "Anti-carcinoembryonic antigen (CEA) diabody for rapid tumor targeting and imaging," Tumor Targeting, 1999, vol. 4, pp. 47-58.
Wu, X. et al., "Immunofluorescent labeling of cancer marker Her2 and other cellular targets with semiconductor quantum dots," Nature Biotechnology, Jan. 2003, vol. 21, pp. 41-46.
Xing, Y. et al., "Bioconjugated quantum dots for multiplexed and quantitativ immunohistochemistry," Nature Protocols, 2007, vol. 2, No. 5, pp. 1152-1165.
Yazaki, P.J. et al., "Mammalian expression and hollow fiber bioreactor production of 34. recombinant anti-CEA diabody and minibody for clinical applications," Journal of Immunological Methods, 2001, vol. 253, pp. 195-208.
Yokota, T. et al., "Rapid Tumor Penetration of a Single-Chain Fv and Comparison with Other Immunoglobulin Forms," Cancer Research, Jun. 15, 1992, vol. 52, pp. 3402-3408.
Adams et al., "Highly specific in vivo tumor targeting by monovalent and divalent forms of 741F8 anti-c-erbB-2 single-chain Fv." Cancer Res. 53.17 (Sep. 1, 1993): 4026-34.

(56) References Cited

OTHER PUBLICATIONS

Albrecht et al., "Development of anti-MUC1 di-scFvs for molecular targeting of epithelial cancers, such as breast and prostate cancers." *Q J Nucl Med Mol Imaging* 51.4 (Dec. 2007): 304-13.

Atwell et al., "scFv multimers of the anti-neuranminidase antibody NC10: length of the linker between $V_H$ and $V_L$ domains dictates precisely the transition between diabodies and triabodies," Protein Engineering, Jul. 1999, vol. 12, No. 7, pp. 597-604.

U.S. Appl. No. 13/554,306, filed Jul. 20, 2012, Wu et al.

Barat et al., "Cys-diabody quantum dot conjugates (immunoQdots) for cancer marker detection." *Bioconjug Chem.* 20.8 (Aug. 19, 2009): 1474-81.

Carmichael et al., "The Crystal Structure of an Anti-CEA scFv Diabody scFvs in V(L)-to-V(H) Orientation: Implications for Diabody Flexibility." *J. Mol. Biol.* 326.2 (Feb. 14, 2003): 341-51.

Communication pursuant to Rules 70(2) and 70a(2) EPC dated Dec. 28, 2010, received in EP Appl. No. 08799192.3, 11 pages.

Desplancq et al., "Multimerization behaviour of single chain Fv variants for the tumour-binding antibody B72.3," Protein Engineering, Aug. 1994, vol. 7, No. 8, pp. 1027-1033.

Fitzgerald et al., "Improved Tumor Targeting by Disulphide Stabilized Diabodies Expressed in Pichia Pastoris." *Protein Engineering* 10.10 (1997): 1221-1225.

Glockshuber et al., "A Comparison of Strategies to Stabilize Immunoglobulin Fv-Fragments." *Biochemistry* 29.6 (1990): 1362-1367.

Hollinger et al., "Diabodies: Small Bivalent and Bispecific Antibody Fragments." *Proc. Natl. Acad. Sci. USA* 90 (Jul. 1993): 6444-6448.

Hu et al., "Minibody: A Novel Engineered Anti-carcinoembryonic Antigen Antibody Fragment (Single-Chain $F_v$-$C_H^3$) Which Exhibits Rapid, High-Level Targeting of Xenografts." *Cancer Research* 56 (Jul. 1, 1996): 3055-3061.

Johnson et al., "Effector cell recruitment with novel Fv-based dual-affinity re-targeting protein leads to potent tumor cytolysis and in vivo B-cell depletion." J Mol Biol. 399.3 (Jun. 11, 2010): 436-49.

Kim et al., "Anti-CD30 diabody-drug conjugates with potent antitumor activity." *Mol Cancer Ther.* 7.8 (Aug. 2008): 2486-97.

Leung et al., "Engineering a Unique Glycosylation Site for Site-Specific Conjugation of Haptens to Antibody Fragments." *The Journal of Immunology* 154 (1995): 5919-5926.

Li et al., "Improved biodistribution and radioimmunoimaging with poly(ethylene glycol)-DOTA-conjugated anti-CEA diabody." *Bioconjug Chem.* 17.1 (Jan.-Feb. 2006): 68-76.

Li et al., "Reduction of Kidney Uptake in Radiometal Labeled Peptide Linkers Conjugated to Recombinant Antibody Fragments, Site-Specific Conjugation of DOTA-Peptides to a Cys-Diabody." *Bioconjugate Chem.* 13.5 2002 : 985-995.

McCartney et al., "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides." *Protein Eng.* 8.3 (Mar. 1995):301-14.

McCartney et al., Refolding of single-chain Fv with C-terminal cysteine (sFv); formation of disulfide-bonded homodimers of antic-A£'r/7B-2 and anti-digoxin sFv', Miami Short Rep., 1993, vol. 3, p. 91.

Moore et al., "Application of dual affinity retargeting molecules to achieve optimal redirected T-cell killing of B-cell lymphoma." *Blood* 117.17 (Apr. 28, 2011): 4542-51.

Olafsen et al., "Covalent Disulfide-linked Anti-CEA Diabody Allows Site-specific Conjugation and Radiolabeling for Tumor Targeting Applications." *Protein Engineering, Design & Selection* 17.1 (2004): 21-27.

Olafsen et al., "ImmunoPET imaging of B-cell lymphoma using 124I-anti-CD20 scFv dimers (diabodies)." *Protein Eng Des Sel.* 23.4 (Apr. 2010): 243-9.

Raag et al., "Single-chain Fvs." FASEB J., Jan. 1995, vol. 9, No. 1, pp. 73-80.

Rudikoff et al., *Proc. Natl. Acad. Sci. USA* 79 (1982): 1979.

Sirk et al., "Site-specific, thiol-mediated conjugation of fluorescent probes to cysteine-modified diabodies targeting CD20 or HER2." *Bioconjug Chem.* 19.12 (Dec. 2008): 2527-34.

Stimmel et al., "Site-Specific Conjugation on Serine Cysteine Variant Monoclonal Antibodies." *The Journal of Biological Chemistry* 275. 39 (Sep. 29, 2000): 30445-30450.

Tai et al., "Targeting c-erbB-2 expressing tumors using single-chain Fv monomers and dimers." *Cancer Res.* 55.23Suppl (Dec. 1, 1995):5983s-5989s.

Verhaar et al., "Technetium-99m Radiolabeling Using a Phage-Derived Single-Chain $F_V$ with a C-Terminal Cysteine." *The Journal of Nuclear Medicine* 37.5 (May 1996): 868-872.

Veri et al., "Therapeutic control of B cell activation via recruitment of Fcgamma receptor IIb (CD32B) inhibitory function with a novel bispecific antibody scaffold." *Arthritis Rheum.* 62.7 (Jul. 2010): 1933-43.

Whitlow et al., "Multivalent Fvs: characterization of single-chain Fv oligomers and preparation of a bispecific Fv," Protein Engineering, Aug. 1994, vol. 7, No. 8, pp. 1017-1026.

Wu et al., "Anti-carcinoembryonic Antigen (CEA) Diabody for Rapid Tumor Targeting and Imaging." *Tumor Targeting* 4 (1999): 47-58.

Wu et al., "High-resolution MicroPET Imaging of Carcino-Embryonic Antigen-Positive Xenografts by Using a Copper-64-Labeled Engineered Antibody Fragment," *Proc. Natl. Acad. Sci. USA*, vol. 97, No. 15, pp. 8495-8500 (2000).

Wu et al., "Tumor localization of Anti-CEA Single-Chain Fvs: Improved Targeting by Non-Covalent Dimers," Immunotechnoloqy, vol. 2, pp. 21-36 (1996).

Yazaki et al., "Mammalian Expression and Hollow Fiber Bioreactor Production of Recombinant Anti-CEA Diabody and Minibody for Clinical Applications." *Journal of Immunological Methods* 253 (2001): 195-208.

Yazaki et al., "Tumor Targeting of Radiometal Labeled Anti-CEA Recombinant T84.66 Diabody and T84.66 Minibody: Comparision to Radioiodinated Fragments." *Bioconjugate Chem.* 12 (2001): 220-228.

You et al., "Expression, Purification, and Characterization of a Two Domain Carcinoembryonic Antigen Minigene (N-A3) in Pichia Pastoris:The Essential Role of the N-Domain." *Anticancer Research* 18(1998): 3193-3202.

City of Hope National Medical Center, "Anti-CEA antibody T84.66 humanized," Medical Imaging Law Weekly, copyright 2004, http://www.newsrx.com/newsletters/Medical-Imaging-Law-Weekly ; dated for online publication Nov. 27, 2004.

George et al., "Radiometal labeling of recombinant proteins by a genetically engineered minimal chelation site: technetium-99m coordination by single-chain Fv antibody fusion proteins through a C-terminal cysteinyl peptide," Proc. Natl. Acad. Sci. USA, Aug. 1995, vol. 92, No. 18, pp. 8358-8362.

Gu et al., "Biological activity and microPET imaging properties of chimeric and humanized anit-prostate stem cell antigen (PSCA) antibodies," Proc Amer Assoc Cancer Res., 2005, vol. 46, Abstract #696 [Retrieved on May 14, 2012], URL: http://aacrmeetingabstracts.org/cgi/content/abstract/2005/1/164-b.

Marty et al., "Production of functionalized single-chain Fv antibody fragments binding to the ED-B domain of the B-isoform of fibronectin in *Pichia pastoris*," Protein Expression and Purification, Feb. 2001, vol. 21, Issue 1, pp. 156-164.

Neumaier et al., "Cloning of the genes for T84.66, and antibody that has a high specificity and affinity for carcinoembryonic antigen, and expression of chimeric human/mouse T84.66 genes in myeloma and Chinese hamster ovary cells," Cancer Research, 1990, vol. 50, pp. 2128-2134.

Preliminary Amendment filed on Dec. 21, 2011 in U.S. Appl. No. 12/788,477 (Filing Date: May 27, 2012) in 9 pages.

Urva et al., "Physiologically based pharmacokinetic (PBPK) model for T.84.66, A monoclonal anti-CEA antibody," Am. Assoc. Pharm. Sci. 10 (Supp. 2), 2008, pp. 957.

File History of U.S. Appl. No. 10/690,990, filed Oct. 23, 2003.

File History of U.S. Appl. No. 12/788,477, filed May 27, 2010.

File History of U.S. Appl. No. 13/554,306, filed Jul. 20, 2012.

Extracts from Janeway and Travers, Immuno. Biology, 3rd Ed. 1997.

(56) References Cited

OTHER PUBLICATIONS

Gu et al., Oncogene, 19: 1288-1296 (2000) Prostrate stem cell antigen (PSCA) expression increases with high gleason score, advanced stage and bone metastasis in prostate cancer.

Hopp and Woods, Mol. Immunol. 20: pp. 483-489 (1983) A computer program for predicting protein antigenic determinants.

Horoszewicz J.S. et. al., Anticancer Res. 7: pp. 927-936, (1987) Monoclonal antibodies to a new antigenic marker in epithelial prostatic cells and serum of prostatic cancer patients.

Olafsen, T. et al., J. Immunother, 30:4 396 (2007) Targeting, Imaging, and Therapy Using a Humanized Antiprostate Stem Cell antigen (PSCA) Antibody.

Persiani S et., al., Cancer Immunol Immunother (1989), 29: pp. 167-170 In vivo antitumor effect of methotrexate conjugated to a monoclonal IgM antibody specific for stage-specific embryonic antigen-1, on MH-15 mouse teratocarcinoma.

Tazzari P.L. et al., Cancer Immunol Immunother (1988) 26: pp. 231-236 An immunotoxin containing a rat IgM monoclonal antibody (Campath 1) and saporin 6: effect on T lymphocytes and hemopoietic cells.

Usui H. et. al., Acta Med Okayama, 1994; 48 (6): pp. 305-309 Evaluation of Ricin a Chain-Containing Immunotoxins Directed Against Glycolipid and Glycoprotein on Mouse Lymphoma Cells.

Wiedloha A. et. al., Archivum Immunologiae et Therapiae Experimentalis, 1989, 37, pp. 101-113 Specific killing of mouse leukemic cells with ricin A-chain immunotoxin.

Wiels J. et. at., Cancer Research 44, pp. 129-133, Jan. 1984 Properties of immunotoxins against a glycolipid antigen associated with Burkitt's lymphoma.

Wu, A.M. et al. "Arming antibodies: prospects and challenges for immunoconjugates." Nature Biotechnology, Sep. 2007, vol. 23: pp. 1137-1146.

Notice of Opposition to European Patent Application No. 0668777 filed Jul. 11, 2007 by BZL Biologics LLC.

Notice of Opposition to European Patent Application No. 0956506 filed Dec. 1, 2006 by PSMA Development Company LLC.

Olafsen, T. Cancer Biotherapy & Radiopharmaceuticals, "Micropet Evaluation of an I-124-Labeled Antibody Fragment (SCFV-FC) in Non-Internalizing (CDP and CD20) Versus Internalizing (HER2 and PSCA) Tumor Antigen Systems" vol. 21, No. 4 (2006).

Barat, B. et al., "Engineered antibody-quantum dot conjugates (immunoQdotes) for cancer marker detection" Abstract Category: Advances in Optical Probes, 1 page, (2010).

Notice of Allowance for U.S. Appl. No. 12/293,860, Wu, A. et al. "Engineered Anti-Prostate Stem Cell Antigen (PSCA) Antibodies for Cancer Targeting" (Date of Notice: Dec. 9, 2014).

* cited by examiner

FIG. 2 (SHEET 1)

```
                1         *        20         *        30         *        40         *        50         *        60
                                                              CDR-L1                                    CDR-L2
P-2B3    DIQLTQSPSSLSASVGDRVTITCSASSSVRFIHWYQQKPGKAPKRLIYDTSKLASGVPSR
         1         *        20         *        30         *        40         *        50         *        60
1. C5    DIQLIQSPSSLSASVGDRVTITCSASSSVRFIHWYQQKPGKAPKRLIYDTSKLASGVPSR
         ||||:||||||||||||||||||||||||||||||||||||||||||||||||||||||
P-2B3    DIQLTQSPSSLSASVGDRVTITCSASSSVRFIHWYQQKPGKAPKRLIYDTSKLASGVPSR
         1         *        20         *        30         *        40         *        50         *        60
2. A2    DIQLTQSPSSLSASVGDRVTITCSASSSVRFIHWYQQKPGKAPKRLIYDTSKLASGVPSR
         ||||||||||||||||||||||||||||||||||||||||||||||||||||||||||||
P-2B3    DIQLTQSPSSLSASVGDRVTITCSASSSVRFIHWYQQKPGKAPKRLIYDTSKLASGVPSR
         1         *        20         *        30         *        40         *        50         *        60
3. A11   DIQLTQSPSTLSASMGDRVTITCSASSSVRFIHWYQQKPGKAPKRLIYDTSKLASGVPSR
         |||||||||:||||:|||||||||||||||||||||||||||||||||||||||||||||
P-2B3    DIQLTQSPSSLSASVGDRVTITCSASSSVRFIHWYQQKPGKAPKRLIYDTSKLASGVPSR

*        70         *        80         *        90         *       100         *       110         *       120
                                                                      CDR-L3
P-2B3    FSGSGSGTDFTLTISSLQPEDFATYYCQQWSSSPFTFGQGTKVEIKGSTSGGGSGGGSGG
           *        70         *        80         *        90         *       100         *       110         *       120
1. C5    FSGSGSGTDFTLTISSLQPEDFATYYCQQWSSSPFTFGQGTKVEIKGSTSGGGSGGGSGG
         ||||||||||||||||||||||||||||||||||||||||||||||||||||||||||||
P-2B3    FSGSGSGTDFTLTISSLQPEDFATYYCQQWSSSPFTFGQGTKVEIKGSTSGGGSGGGSGG
           *        70         *        80         *        90         *       100         *       110         *       120
2. A2    FSGSGSGTDFTLTISSLQPEDFATYYCQQWSSSPFTFGQGTKVEIKGSTSGGGSGGGSGG
         ||||||||||||||||||||||||||||||||||||||||||||||||||||||||||||
P-2B3    FSGSGSGTDFTLTISSLQPEDFATYYCQQWSSSPFTFGQGTKVEIKGSTSGGGSGGGSGG
           *        70         *        80         *        90         *       100         *       110         *       120
3. A11   FSGSGSGTDFTLTISSLQPEDFATYYCQQWGSSPFTFGQGTKVEIKGSTSGGGSGGGSGG
         |||||||||||||||||||||||||||||:||||||||||||||||||||||||||||||
P-2B3    FSGSGSGTDFTLTISSLQPEDFATYYCQQWSSSPFTFGQGTKVEIKGSTSGGGSGGGSGG
```

Fig. 2 (sheet 2)

```
              130        *        140        *        150        *        160        *        170        *        180        *        190
P-2B3  GGSSEVQLVESGGGLVQPGGSLRLSCAASGFNIKDYYIHWVRQAPGKGLEWVAWIDPENGDTEFVPKFQG
                                              CDR-H1                        CDR-H2
              130        *        140        *        150        *        160        *        170        *        180        *        190
1. C5  GGSSEVQLVESGGGLVQPGGSLRLSCAASGFNIKDYYIHWVRQAPGKGLEWVAWIDPENGDTEFVPKFQG
P-2B3  ----------------------------------------------------------------------
              130        *        140        *        150        *        160        *        170        *        180        *        190
2. A2  GG-SEVQLVESGGGLVQPGGSLRLSCAASGFNIKDYYIHWVRQAPGKGLEWVAWIDPEYGDSEFVPKFQG
P-2B3  ----------------------------------------------------------------------
              130        *        140        *        150        *        160        *        170        *        180        *        190
3. A11 GGSSEVQLVEYGGGLVQPGGSLRLSCAASGFNIKDYYIHWVRQAPGKGLEWVAWIDPENGDTEFVPKFQG
P-2B3  ----------------------------------------------------------------------

*        200        *        210        *        220        *        230        *        240
P-2B3  RATISADTSKNTAYLQMNSLRAEDTAVYYCKTGGFWGQGTLVTVSSAAG    (SEQ ID NO:4)
                                            CDR-H3
          *        200        *        210        *        220        *        230        *        240
1. C5  RATISADTSKNTVYLQMNSLRAKDTAVYYCKTGGFWGQGTLVTVSSAAG    (SEQ ID NO:5)
P-2B3  ------------------------------------------------    (SEQ ID NO:4)
          *        200        *        210        *        220        *        230        *        240
2. A2  RATMSADTSKNTAYLQMNSLRAEDTAVYYCKTGGFWGRGTLVTVSSAAG    (SEQ ID NO:6)
P-2B3  ------------------------------------------------    (SEQ ID NO:4)
          *        200        *        210        *        220        *        230        *        240
3. A11 RATMSADTSKNTAYLQMNSLRAEDTAVYYCKTGGFWGQGTLVTVSSAAG    (SEQ ID NO:7)
P-2B3  ------------------------------------------------    (SEQ ID NO:4)
```

Fig. 3 (sheet 1)

```
tctagagccgccaccatggagacagacactcctgctctatggtgtgctgctctggtt
  S  R  A  A  T  M  E  T  D  T  L  L  L  W  V  L  L  L  W  V
```
*signal peptide*
```
ccaggttccaccggtgacattcagctgacccaatctccaagctctttgtccgcctctgtg
  P  G  S  T  G  D  I  Q  L  T  Q  S  P  S  S  L  S  A  S  V ggggatagggtcaccatcacctgcagtgccagttcaagtgtaagattcattcactggtac
  G  D  R  V  T  I  T  C  S  A  S  S  S  V  R  F  I  H  W  Y cagcagaaaccaggaaaagctcccaaagactcatctatgacacatccaaactggcttct
  Q  Q  K  P  G  K  A  P  K  R  L  I  Y  D  T  S  K  L  A  S ggcgtccctctaggttctcagtggctccgggacagacttcaccctcaccattagc
  G  V  P  S  R  P  S  G  S  G  T  D  F  T  L  T  I  S agtctgcagccggaagatttcgccacttattactgtcagcagtggagtagccattc
  S  L  Q  P  E  D  F  A  T  Y  Y  C  Q  Q  W  S  S  P  F acgttcggacaggggaccaaggtggagataaaggcagtactagcggcggtggctccgga
  T  F  G  Q  G  T  K  V  E  I  K  G  S  T  S  G  G  G  S  G
```
*linker*

Fig. 3 (sheet 2)

```
ggcggctccggaggtggcggcagctcagaggttcagctggtggagtctgggggtggcctt
 G  G  S  G  G  G  G  S  S  E  V  Q  L  V  E  S  G  G  G  L
                               V_H
gtgcagccagggggcctcactccgttttgtctgcgcagcttctggcttcaacattaaagac
 V  Q  P  G  G  S  L  R  L  S  C  A  A  S  G  F  N  I  K  D
tactatatacactgggtgcgtcaggccccctggtaagggcctggaatgggttgcatggatt
 Y  Y  I  H  W  V  R  Q  A  P  G  K  G  L  E  W  V  A  W  I
gatcctgagaatggtgacactgaatttgtcccgaagttccagggccgtgccactataagc
 D  P  E  N  G  D  T  E  F  V  P  K  F  Q  G  R  A  T  I  S
gatcctgagaatggtgacactgaatttgtcccgaagttccagggccgtgccactataagc
 A  D  T  S  K  N  T  A  Y  L  Q  M  N  S  L  R  A  E  D  T
gccgtctattattgtaaaacgggggggttctggggtcaaggaaccctggtcaccgtctcg
 A  V  Y  Y  C  K  T  G  G  F  W  G  Q  G  T  L  V  T  V  S
agcgagcccaaatctttgtgacaaaactcacacatgccaccgtgcggcggaggtagctct
 S  E  P  K  S  C  D  K  T  H  T  C  P  P  C  G  G  G  S  S
              hinge                                 extension
```

Fig. 3 (sheet 3)

```
ggcggtggatccggggcagccccgagaaccacaggtgtacaccctgcccccatcccgg
 G  G  S  G  G  Q  P  R  E  P  Q  V  Y  T  L  P  P  S  R
                   C_HJ
gatgagctgaccaagaaccaggtcagcctgacctgcctggtcaaaggcttctatcccagc
 D  E  L  T  K  N  Q  V  S  L  T  C  L  V  K  G  F  Y  P  S
gacatcgccgtggagtgggagagcaatgggcagccggagaacaactacaagaccacgcct
 D  I  A  V  E  W  E  S  N  G  Q  P  E  N  N  Y  K  T  T  P
cccgtgctggactccgacggctccttcttcctctacagcaagctcaccgtggacaagagc
 P  V  L  D  S  D  G  S  F  F  L  Y  S  K  L  T  V  D  K  S
aggtggcagcaggggaacgtcttctcatgctccgtgatgcatgaggctctgcacaaccac
 R  W  Q  Q  G  N  V  F  S  C  S  V  M  H  E  A  L  H  N  H
tacacgcagaagagcctctccctgtctccgggtaaatgatag
 Y  T  Q  K  S  L  S  L  S  P  G  K  -  -
```

Fig. 4

| (kDa) | M | P | A11 | C5 | A2 |
|---|---|---|---|---|---|
| 214.9 | | | | | |
| 132.4 | | | | | ↓ |
| 85.4 | | | | | |
| 40.4 | | | | | |
| 31.3 | | | | | |

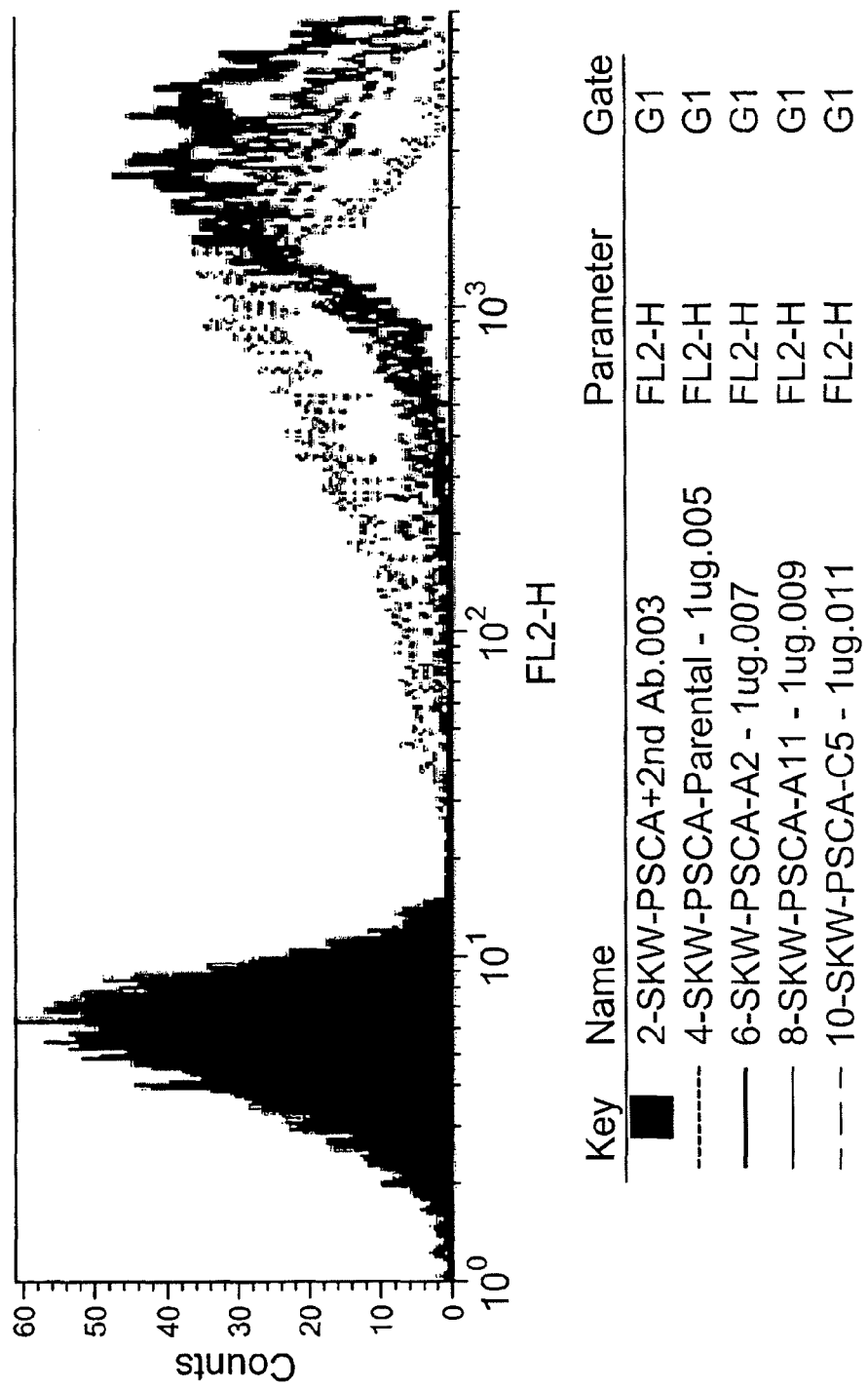

Fig. 8

|  | Tumor/blood Biodistribution | Tumor/background MicroPET |
|---|---|---|
| A2 | 0.67 | 2.9 |
| A11 | 1.08 | 8.5 |
| C5 | 0.73 | 2.9 |

|  | Tumor/blood Biodistribution | Tumor/background MicroPET |
|---|---|---|
| Parental | 0.88 | 2.4 |
| A11 | 1.11 | 5.8 |

Prostate Stem Cell Antigen (PSCA)

Gleason 4 prostate cancer
stained with 1GB anti-PSCA Ab

R. Reiter et al., PNAS 1998
Saffran et al., PNAS 2000
Z Gu et al., Oncogene 2000

123 a.a GPI-linked cell surface protein expressed in prostate and bladder

Over expressed in prostate cancer (40% localized, 60-100% metastatic cancer), bladder, and pancreatic cancer Murine anti-PSCA antibody biologically active (1G8)

Fig. 10
Anti-PSCA Antibodies and Antibody Fragments
1) 1G8: mouse monoclonal antibody (150 kDa)
   (Gu Z, et al., Oncogene 2000)
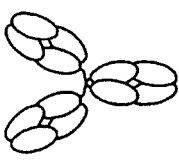
2) 2B3: humanized 1G8
   (Olafsen T, et al. Imunother 2007)
3) 2B3 antibody fragments:
   - ScVF: 28kDA 
   - Diabody: 55kDa 
   - Minibody: 80kDa 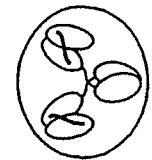   2B3 parental (P) minibody has shown better tumor targeting
   - ScFv-Fc: 110kDa 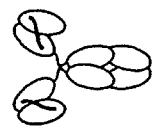

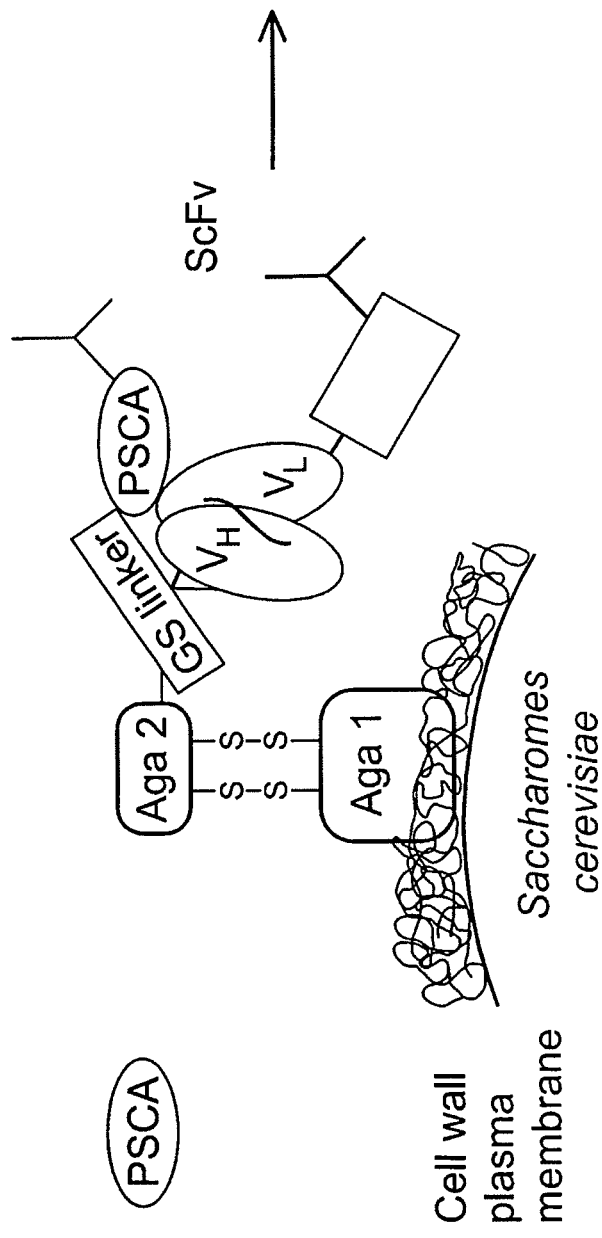
Fig. 11 (sheet 1)

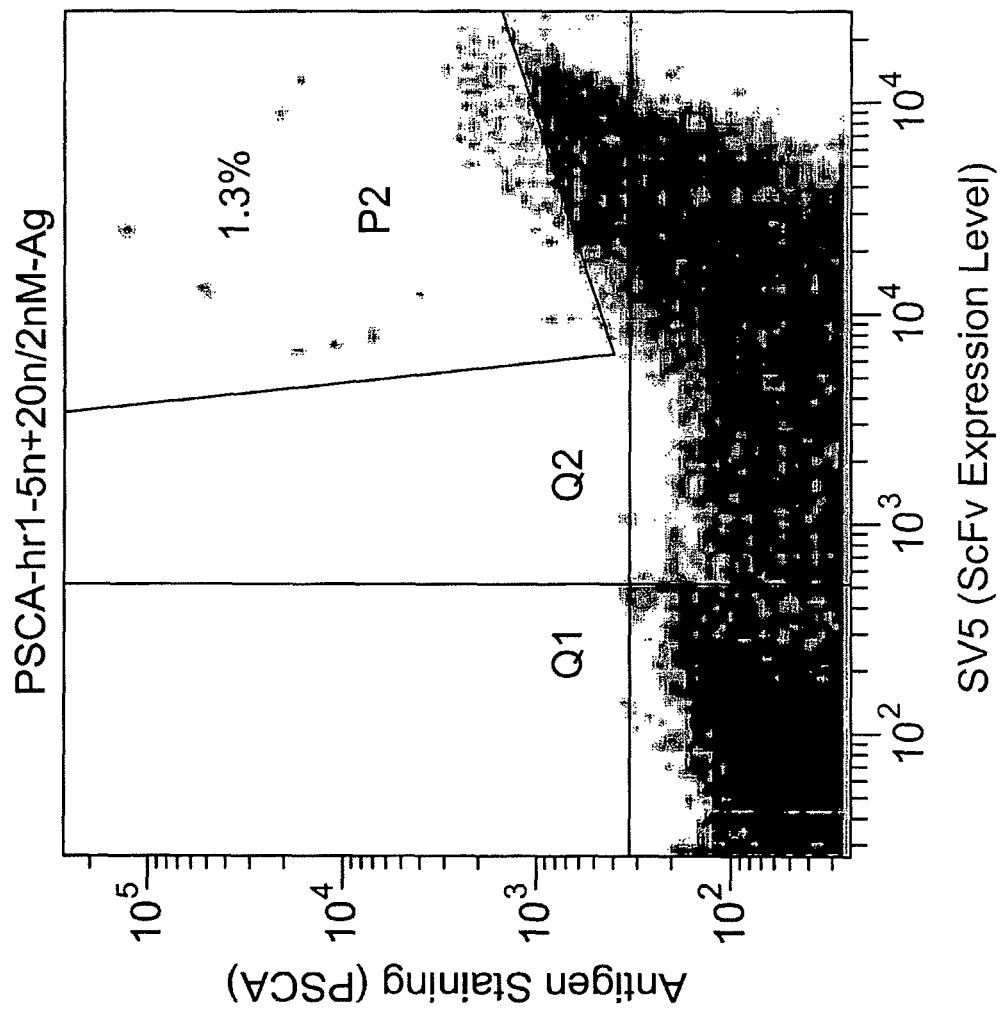
Fig. 11 (sheet 2)

MicroPET Imaging and Biodistribution:
Three 2B3 Affinity Variant Minibodies

Image rendering with the same max and min threshold
(max = 2.0164e-05, min = 1.388e-05)

|  | A2 | A11 | C5 |
|---|---|---|---|
| Tumor/blood (Biodistribution at 25 h) | 0.67 | 1.08 | 0.73 |
| Tumor/background MicroPET imaging at 20 h | 2.9 | 8.5 | 2.9 |

MicroPET Imaging and Biodistribution: Parental and A11

PET Imaging of Capan-1 Xenografts

Fig. 15
PET Imaging of MIA PaCa-2 Xenografts

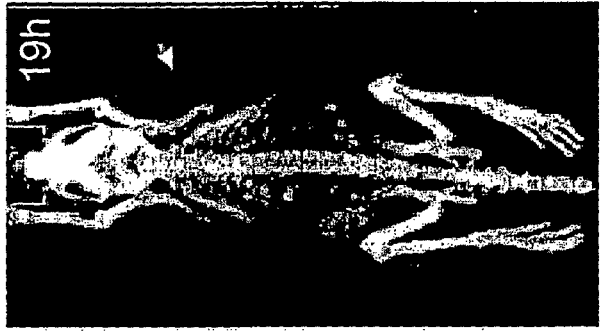

200 μg pMb labeled with I-124
Labeling efficiency: 71.2 – 76.6%
Specific activity: 2.0 – 2.7 μCi/g
Immunoreactivity: 28%
Injected activity: 138 – 141 μCi 300 μg affMb labeled with I-124
Labeling efficiency: 73.3%
Specific activity: 1.9 μCi/g
Immunoreactivity: 8.2%
Injected activity: 109 – 114 μCi $^{124}$I-Parental Mb
Tumor uptake (n=4) 0.80(0.39)% ID/g
Tumor to soft tissue ratio: 1.3

$^{124}$I-Affinity matured Mb
Tumor uptake (n=4) 0.81(0.25)% ID/g
Tumor to soft tissue ratio: 2.1

Fig. 16a (sheet 1)
2B3 affinity Various Protein Sequences

2B3 parental minibody sequence

DIQLT

Fig. 16a (sheet 2)

2B3 A11 minibody sequence

DIQLTQSPSTLSASMGDRVTITCSASSSVRFIHW
YQQKPGKAPKRLIYDTSKLASGVPSRFSGSGSG
TDFTLTISSLQPEDFATYYCQQWGSSPFTFGQG
TKVEIKGSTSGGGSGGGGSGGGGSSEVQLVEYGG
GLVQPGGSLRLSCAASGFNIKDYYIHWVRQAPG
KGLEWVAWIDPENGDTEFVPKFQGRATMSADT
SKNTAYLQMNSLRAEDTAVYYCKTGGFWGQGT
LVTVSSEPKSCDKTHTCPPCGGGSSGGGSGGQP
REPQVYTLPPSRDELTKNQVSLTCLVKGFYPSD
IAVEWESNGQPENNYKTTPPVLDSDGSFFLYSK
LTVDKSRWQQGNVFSCSVMHEALHNHYTQKSL
SLSPGK (SEQ ID NO:12)

*Fig. 16b*

2B3 C5 minibody sequence

DIQLIQSPSSLSASVGDRVTITCSASSSVRFIHW
YQQKPGKAPKRLIYDTSKLASGVPSRFSGSGSG
TDFTLTISSLQPEDFATYYCQQWSSSPFTFGQGT
KVEIKGSTSGGGSGGGGSGGGGSSEVQLVESGGG
LVQPGGSLRLSCAASGFNIKDYYIHWVRQAPGK
GLEWVAWIDPENGDTEFVPKFQGRATISADTSK
NTVYLQMNSLRAKDTAVYYCKTGGFWGQGTLV
TVSSEPKSCDKTHTCPPCGGGSSGGGSGGQPRE
PQVYTLPPSRDELTKNQVSLTCLVKGFYPSDIA
VEWESNGQPENNYKTTPPVLDSDGSFFLYSKLT
VDKSRWQQGNVFSCSVMHEALHNHYTQKSLSL
SPGK (SEQ ID NO:13)

SEQUENCE LISTING

```
<160> NUMBER OF SEQ ID NOS: 13

<210> SEQ ID NO 1
<211> LENGTH: 123
<212> TYPE: PRT
<213> ORGANISM: homo sapiens

<400> SEQUENCE: 1

Met Lys Ala Val Leu Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ala Ile Leu Ala Leu Leu Pro Ala
            100                 105                 110
```

```
Leu Gly Leu Leu Leu Trp Gly Pro Gly Gln Leu
        115                 120
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      oligonucleotide Gap 5' for construction of mutant scFv yeast
      display vector pYD2 library

<400> SEQUENCE: 2
ttaagcttct gcaggctagt g                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      oligonucleotide Gap 3' for construction of mutant scFv yeast
      display vector pYD2 library

<400> SEQUENCE: 3
gagaccgagg agagggttag g                                              21

<210> SEQ ID NO 4
<211> LENGTH: 239
<212> TYPE: PRT
<213> ORGANISM: Artificial Sequence
<220> FEATURE:
<223> OTHER INFORMATION: Description of Artificial Sequence:humanized
      mouse monoclonal anti-PSCA 1G8 antibody (Trastuzumab, 2B3)
      parental P-2B3 wild type scFv

<400> SEQUENCE: 4

```
Asp Ile Gln Leu Thr Gln Ser Pro Ser Leu Ser Ala Ser Val Gly
1               5                   10                  15

Asp Arg Val Thr Ile Thr Cys Ser Ala Ser Ser Ser Val Arg Phe Ile
                20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190
```

```
Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
        210                 215                 220

Phe Trp Gly Gln Gly Thr Leu Val Thr Val Ser Ser Ala Ala Gly
225                 230                 235
```

<210> SEQ ID NO 5
<211> LENGTH: 239
<212> TYPE: PRT
<213> ORGANISM: Artificial Sequence
<220> FEATURE:
<223> OTHER INFORMATION: Description of Artificial Sequence:humanized
      mouse monoclonal anti-PSCA 1G8 antibody (Trastuzumab, 2B3)
      affinity variant mutant C5 scFv

<400> SEQUENCE: 5

```
Asp Ile Gln Leu Ile Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Pro Phe Thr
                85                  90                  95

Phe Gly Gln Gly Thr Lys Val Glu Ile Lys Gly Ser Thr Ser Gly Gly
                100                 105                 110

Gly Ser Gly Gly Gly Ser Gly Gly Gly Ser Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Ile Ser Ala Asp Thr Ser Lys Asn Thr Val Tyr Leu Gln Met Asn
        195                 200                 205

Ser Leu Arg Ala Lys Asp Thr Ala Val Tyr Tyr Cys Lys Thr Gly Gly
        210                 215                 220

Phe Trp Gly Gln Gly Thr Leu Val Thr Val Ser Ser Ala Ala Gly
225                 230                 235
```

<210> SEQ ID NO 6
<211> LENGTH: 238
<212> TYPE: PRT
<213> ORGANISM: Artificial Sequence
<220> FEATURE:
<223> OTHER INFORMATION: Description of Artificial Sequence:humanized
      mouse monoclonal anti-PSCA 1G8 antibody (Trastuzumab, 2B3)
      affinity variant mutant A2 scFv

<400> SEQUENCE: 6

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Gly Ser Ser Pro Phe Thr
                85                  90                  95

Phe Gly Gln Gly Thr Lys Val Glu Ile Lys Gly Ser Thr Ser Gly Gly
                100                 105                 110

Gly Ser Gly Gly Gly Ser Gly Gly Gly Ser Glu Val Gln

```
                115                 120                 125
Val Glu Tyr Gly Gly Gly Leu Val Gln Pro Gly Gly Ser Leu Arg Leu
        130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Met Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
    210                 215                 220

Phe Trp Gly Gln Gly Thr Leu Val Thr Val Ser Ser Ala Ala Gly
225                 230                 235

<210> SEQ ID NO 8
<211> LENGTH: 1182
<212> TYPE: DNA
<213> ORGANISM: Artificial Sequence
<220> FEATURE:
<223> OTHER INFORMATION: Description of Artificial Sequence:humanized
      mouse monoclonal anti-PSCA 1G8 antibody (Trastuzumab, 2B3)
      parental 2B3 wild type minibody coding sequence with signal
      peptide
<220> FEATURE:
<221> NAME/KEY: CDS
<222> LOCATION: (1)..(1179)
<223> OTHER INFORMATION: parental 2B3 minibody with signal peptide

<400> SEQUENCE: 8 tct aga gcc gcc acc atg gag aca gac aca ctc ctg cta tgg gtg ctg      48
Ser Arg Ala Ala Thr Met Glu Thr Asp Thr Leu Leu Leu Trp Val Leu
1               5                   10                  15 ctg ctc tgg gtt cca ggt tcc acc ggt gac att cag ctg acc caa tct      96
Leu Leu Trp Val Pro Gly Ser Thr Gly Asp Ile Gln Leu Thr Gln Ser
            20                  25                  30 cca agc tct ttg tcc gcc tct gtg ggg gat agg gtc acc atc acc tgc     144
Pro Ser Ser Leu Ser Ala Ser Val Gly Asp Arg Val Thr Ile Thr Cys
        35                  40                  45 agt gcc agt tca agt gta aga ttc att cac tgg tac cag cag aaa cca     192
Ser Ala Ser Ser Ser Val Arg Phe Ile His Trp Tyr Gln Gln Lys Pro
    50                  55                  60 gga aaa gct ccc aaa aga ctc atc tat gac aca tcc aaa ctg gct tct     240
Gly Lys Ala Pro Lys Arg Leu Ile Tyr Asp Thr Ser Lys Leu Ala Ser
65                  70                  75                  80 ggc gtc cct tct agg ttc agt ggc tcc ggg tct ggg aca gac ttc acc     288
Gly Val Pro Ser Arg Phe Ser Gly Ser Gly Ser Gly Thr Asp Phe Thr
                85                  90                  95 ctc acc att agc agt ctg cag ccg gaa gat ttc gcc acc tat tac tgt     336
Leu Thr Ile Ser Ser Leu Gln Pro Glu Asp Phe Ala Thr Tyr Tyr Cys
            100                 105                 110 cag cag tgg agt agt agc cca ttc acg ttc gga cag ggg acc aag gtg     384
Gln Gln Trp Ser Ser Ser Pro Phe Thr Phe Gly Gln Gly Thr Lys Val
        115                 120                 125 gag ata aaa ggc agt act agc ggc ggt ggc tcc gga ggc ggc tcc gga     432
Glu Ile Lys Gly Ser Thr Ser Gly Gly Gly Ser Gly Gly Gly Ser Gly
    130                 135                 140 ggt ggc ggc agc tca gag gtt cag ctg gtg gag tct ggg ggt ggc ctt     480
Gly Gly Gly Ser Ser Glu Val Gln Leu Val Glu Ser Gly Gly Gly Leu
145                 150                 155                 160
```

-continued

```
gtg cag cca ggg ggc tca ctc cgt ttg tcc tgc gca gct tct ggc ttc    528
Val Gln Pro Gly Gly Ser Leu Arg Leu Ser Cys Ala Ala Ser Gly Phe
            165                 170                 175 aac att aaa gac tac tat ata cac tgg gtg cgt cag gcc cct ggt aag    576
Asn Ile Lys Asp Tyr Tyr Ile His Trp Val Arg Gln Ala Pro Gly Lys
        180                 185                 190 ggc ctg gaa tgg gtt gca tgg att gat cct gag aat ggt gac act gaa    624
Gly Leu Glu Trp Val Ala Trp Ile Asp Pro Glu Asn Gly Asp Thr Glu
    195                 200                 205 ttt gtc ccg aag ttc cag ggc cgt gcc act ata agc gca gac aca tcc    672
Phe Val Pro Lys Phe Gln Gly Arg Ala Thr Ile Ser Ala Asp Thr Ser
210                 215                 220 aaa aac aca gcc tac ctg cag atg aac agc ctg cgt gct gag gac act    720
Lys Asn Thr Ala Tyr Leu Gln Met Asn Ser Leu Arg Ala Glu Asp Thr
225                 230                 235                 240 gcc gtc tat tat tgt aaa acg ggg ggg ttc tgg ggt caa gga acc ctg    768
Ala Val Tyr Tyr Cys Lys Thr Gly Gly Phe Trp Gly Gln Gly Thr Leu
                245                 250                 255 gtc acc gtc tcg agc gag ccc aaa tct tgt gac aaa act cac aca tgc    816
Val Thr Val Ser Ser Glu Pro Lys Ser Cys Asp Lys Thr His Thr Cys
            260                 265                 270 cca ccg tgc ggc gga ggt agc tct ggc ggt gga tcc ggc ggg cag ccc    864
Pro Pro Cys Gly Gly Gly Ser Ser Gly Gly Gly Ser Gly Gly Gln Pro
        275                 280                 285 cga gaa cca cag gtg tac acc ctg ccc cca tcc cgg gat gag ctg acc    912
Arg Glu Pro Gln Val Tyr Thr Leu Pro Pro Ser Arg Asp Glu Leu Thr
    290                 295                 300 aag aac cag gtc agc ctg acc tgc ctg gtc aaa ggc ttc tat ccc agc    960
Lys Asn Gln Val Ser Leu Thr Cys Leu Val Lys Gly Phe Tyr Pro Ser
305                 310                 315                 320 gac atc gcc gtg gag tgg gag agc aat ggg cag ccg gag aac aac tac   1008
Asp Ile Ala Val Glu Trp Glu Ser Asn Gly Gln Pro Glu Asn Asn Tyr
                325                 330                 335 aag acc acg cct ccc gtg ctg gac tcc gac ggc tcc ttc ttc ctc tac   1056
Lys Thr Thr Pro Pro Val Leu Asp Ser Asp Gly Ser Phe Phe Leu Tyr
            340                 345                 350 agc aag ctc acc gtg gac aag agc agg tgg cag cag ggg aac gtc ttc   1104
Ser Lys Leu Thr Val Asp Lys Ser Arg Trp Gln Gln Gly Asn Val Phe
        355                 360                 365 tca tgc tcc gtg atg cat gag gct ctg cac aac cac tac acg cag aag   1152
Ser Cys Ser Val Met His Glu Ala Leu His Asn His Tyr Thr Gln Lys
    370                 375                 380 agc ctc tcc ctg tct ccg ggt aaa tga tag                            1182
Ser Leu Ser Leu Ser Pro Gly Lys
385                 390
```

<210> SEQ ID NO 9
<211> LENGTH: 392
<212> TYPE: PRT
<213> ORGANISM: Artificial Sequence
<220> FEATURE:
<223> OTHER INFORMATION: Synthetic Construct

<400> SEQUENCE: 9

```
Ser Arg Ala Ala Thr Met Glu Thr Asp Thr Leu Leu Leu Trp Val Leu
1               5                   10                  15

Leu Leu Trp Val Pro Gly Ser Thr Gly Asp Ile Gln Leu Thr Gln Ser
            20                  25                  30

Pro Ser Ser Leu Ser Ala Ser Val Gly Asp Arg Val Thr Ile Thr Cys
        35                  40                  45
```

Ser Ala Ser Ser Ser Val Arg Phe Ile His Trp Tyr Gln Gln Lys Pro
 50                  55                  60

Gly Lys Ala Pro Lys Arg Leu Ile Tyr Asp Thr Ser Lys Leu Ala Ser
 65                  70                  75                  80

Gly Val Pro Ser Arg Phe Ser Gly Ser Gly Ser Gly Thr Asp Phe Thr
                 85                  90                  95

Leu Thr Ile Ser Ser Leu Gln Pro Glu Asp Phe Ala Thr Tyr Tyr Cys
             100                 105                 110

Gln Gln Trp Ser Ser Ser Pro Phe Thr Phe Gly Gln Gly Thr Lys Val
         115                 120                 125

Glu Ile Lys Gly Ser Thr Ser Gly Gly Gly Ser Gly Gly Gly Ser Gly
     130                 135                 140

Gly Gly Ser Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Phe
                165                 170                 175

Asn Ile Lys Asp Tyr Tyr Ile His Trp Val Arg Gln Ala Pro Gly Lys
            180                 185                 190

Gly Leu Glu Trp Val Ala Trp Ile Asp Pro Glu Asn Gly Asp Thr Glu
        195                 200                 205

Phe Val Pro Lys Phe Gln Gly Arg Ala Thr Ile Ser Ala Asp Thr Ser
210                 215                 220

Lys Asn Thr Ala Tyr Leu Gln Met Asn Ser Leu Arg Ala Glu Asp Thr
225                 230                 235                 240

Ala Val Tyr Tyr Cys Lys Thr Gly Gly Phe Trp Gly Gln Gly Thr Leu
                245                 250                 255

Val Thr Val Ser Ser Glu Pro Lys Ser Cys Asp Lys Thr His Thr Cys
            260                 265                 270

Pro Pro Cys Gly Gly Gly Ser Gly Gly Gly Ser Gly Gly Gln Pro
        275                 280                 285

Arg Glu Pro Gln Val Tyr Thr Leu Pro Pro Ser Arg Asp Glu Leu Thr
    290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
                325                 330                 335

Lys Thr Thr Pro Pro Val Leu Asp Ser Asp Gly Ser Phe Phe Leu Tyr
            340                 345                 350

Ser Lys Leu Thr Val Asp Lys Ser Arg Trp Gln Gln Gly Asn Val Phe
        355                 360                 365

Ser Cys Ser Val Met His Glu Ala Leu His Asn His Tyr Thr Gln Lys
370                 375                 380

Ser Leu Ser Leu Ser Pro Gly Lys
385                 390

<210> SEQ ID NO 10
<211> LENGTH: 367
<212> TYPE: PRT
<213> ORGANISM: Artificial Sequence
<220> FEATURE:
<223> OTHER INFORMATION: Description of Artificial Sequence:humanized
      mouse monoclonal anti-PSCA 1G8 antibody (Trastuzumab, 2B3)
      parental 2B3 wild type minibody

<400> SEQUENCE: 10

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Ile Ser Ala Asp Thr Ser Lys Asn Thr Ala Tyr Leu Gln Met Asn
            195                 200                 205

Ser Leu Arg Ala Glu Asp Thr Ala Val Tyr Tyr Cys Lys Thr Gly Gly
    210                 215                 220

Phe Trp Gly Gln Gly Thr Leu Val Thr Val Ser Ser Glu Pro Lys Ser
225                 230                 235                 240

Cys Asp Lys Thr His Thr Cys Pro Pro Cys Gly Gly Ser Ser Gly
                245                 250                 255

Gly Gly Ser Gly Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
    275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
            355                 360                 365

<210> SEQ ID NO 11
<211> LENGTH: 366
<212> TYPE: PRT
<213> ORGANISM: Artificial Sequence
<220> FEATURE:
<223> OTHER INFORMATION: Description of Artificial Sequence:anti-PSCA
      minibody affinity variant A2

<400> SEQUENCE: 11
```

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65              70                  75                  80

Asp Phe Ala Thr Tyr Tyr Cys Gln Gln Trp Gly Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Glu Val Gln Leu Val
            115                 120                 125

Glu Ser Gly Gly Gly Leu Val Gln Pro Gly Gly Ser Leu Arg Leu Ser
        130                 135                 140

Cys Ala Ala Ser Gly Phe Asn Ile Lys Asp Tyr Tyr Ile His Trp Val
145                 150                 155                 160

Arg Gln Ala Pro Gly Lys Gly Leu Glu Trp Val Ala Trp Ile Asp Pro
                165                 170                 175

Glu Tyr Gly Asp Ser Glu Phe Val Pro Lys Phe Gln Gly Arg Ala Thr
            180                 185                 190

Met Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Lys Thr Gly Gly Phe
210                 215                 220

Trp Gly Arg Gly Thr Leu Val Thr Val Ser Ser Glu Pro Lys Ser Cys
225                 230                 235                 240

Asp Lys Thr His Thr Cys Pro Pro Cys Gly Gly Ser Ser Gly Gly
                245                 250                 255

Gly Ser Gly Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
        290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
            355                 360                 365

<210> SEQ ID NO 12
<211> LENGTH: 367
<212> TYPE: PRT
<213> ORGANISM: Artificial Sequence
<220> FEATURE:
<223> OTHER INFORMATION: Description of Artificial Sequence:anti-PSCA
      minibody affinity variant A11
```

<400> SEQUENCE: 12

```
Asp Ile Gln Leu Thr Gln Ser Pro Ser Thr Leu Ser Ala Ser Met Gly
1               5                   10                  15

Asp Arg Val Thr Ile Thr Cys Ser Ala Ser Ser Val Arg Phe Ile
            20                  25                  30

His Trp Tyr Gln Gln Lys Pro Gly Lys Ala Pro Lys Arg Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Gly Ser Ser Pro Phe Thr
                85                  90                  95

Phe Gly Gln Gly Thr Lys Val Glu Ile Lys Ser Ser Gly Gly
            100                 105                 110

Gly Ser Gly Gly Gly Ser Gly Gly Gly Ser Ser Glu Val Gln Leu
            115                 120                 125

Val Glu Tyr Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Met Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
    210                 215                 220

Phe Trp Gly Gln Gly Thr Leu Val Thr Val Ser Ser Glu Pro Lys Ser
225                 230                 235                 240

Cys Asp Lys Thr His Thr Cys Pro Pro Cys Gly Gly Gly Ser Ser Gly
                245                 250                 255

Gly Gly Ser Gly Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365

<210> SEQ ID NO 13
<211> LENGTH: 367
<212> TYPE: PRT
<213> ORGANISM: Artificial Sequence
<220> FEATURE:
<223> OTHER INFORMATION: Description of Artificial Sequence:anti-PSCA
      minibody affinity variant C5
```

```
<400> SEQUENCE: 13

Asp Ile Gln Leu Ile Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Ser Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
                165                 170                 175

Pro Glu Asn Gly Asp Thr Glu Phe Val Pro Lys Phe Gln Gly Arg Ala
            180                 185                 190

Thr Ile Ser Ala Asp Thr Ser Lys Asn Thr Val Tyr Leu Gln Met Asn
        195                 200                 205

Ser Leu Arg Ala Lys Asp Thr Ala Val Tyr Tyr Cys Lys Thr Gly Gly
    210                 215                 220

Phe Trp Gly Gln Gly Thr Leu Val Thr Val Ser Ser Glu Pro Lys Ser
225                 230                 235                 240

Cys Asp Lys Thr His Thr Cys Pro Pro Cys Gly Gly Gly Ser Ser Gly
                245                 250                 255

Gly Gly Ser Gly Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365
```

HIGH AFFINITY ANTI-PROSTATE STEM CELL ANTIGEN (PSCA) ANTIBODIES FOR CANCER TARGETING AND DETECTION

STATEMENT AS TO RIGHTS TO INVENTIONS MADE UNDER FEDERALLY SPONSORED RESEARCH OR DEVELOPMENT

This invention was made with Government support of Grant No. CA092131, awarded by the NIH/NCI. The Government has certain rights in this invention.

CROSS-REFERENCES TO RELATED APPLICATIONS

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Prostate stem cell antigen (PSCA) a cell surface glycoprotein expressed in normal human prostate and bladder is overexpressed in prostate cancers (40% of primary tumors and 60-100% of lymph node and bone marrow metastases). It is also highly expressed in transitional carcinomas of the bladder and pancreatic carcinoma. 1G8, an anti-PSCA mouse monoclonal antibody specific for PSCA demonstrated antitumor targeting activity in vivo (Gu Z, et al. Cancer Res. 2005; 65:9495). This antibody was humanized by grafting on a human framework (Trastuzumab) and named 2B3 (Olafsen T, et al. J. Immunotherapy 2007; 30:396).

The invention addresses the need for agents that have appropriate pharmacodynamic properties to target and image tumors that express PSCA. There is a tremendous need in the field for effective agents to image cancers with sensitivity and specificity, particularly early stage tumors or ones with early metastasis not imagable by traditional means. As PSCA is highly expressed by most prostate, bladder and pancreatic tumors, it is an important target in the detection, diagnosis, prognosis, and treatment of these cancers. The current invention describes an innovative constructs with optimal characteristics for tumor imaging and targeting. They may also be used for tumor targeting of gene therapy, radioactivity therapy, and may have therapeutic utility by themselves.

BRIEF SUMMARY OF THE INVENTION

This invention describes engineered antibodies that recognize a novel cell surface marker in prostate and other cancers with high affinity. These genetically engineered antibody fragments are tailored specifically for in vivo use for targeting and detection.

The invention addresses the need for agents that have appropriate pharmacodynamic properties to target and image tumors that express PSCA. There is a tremendous need in the field for effective agents to image cancers with sensitivity and specificity, particularly early stage tumors or ones with early metastasis not imagable by traditional means. PSCA is highly expressed by most prostate, bladder and pancreatic tumors and is a promising target. The current invention describes an innovative molecule with optimal characteristics for tumor imaging. It may also be useful for tumor targeting of gene therapy, radioactivity or may have therapeutic utility by itself.

There are multiple embodiments. For instance, there are a variety of engineered antibody formats, such as scFvs, diabodies, triabodies, minibodies, and scFv-Fc. In general, the agent should at least demonstrate bivalent, as opposed to monovalent binding. The overall size, shape, and domain composition of the agent can be varied to suit the final application. Engineered fragments that exhibit optimal targeting in humans may be slightly different from formats that are optimal in mice. Since one goal is human application, the invention incorporates a humanized set of antibody variable regions, as well as human hinge and constant regions. Additional embodiments would include fully human variable regions. The proteins can be expressed in a variety of systems, including microbial, insect cells, mammalian cell culture and transgenic animals.

For imaging purposes, a variety of radionuclides can be attached to the engineered antibodies for detection with gamma or SPECT cameras, or PET scanners. For therapy one can attach drugs, toxins, cytokines, enzymes, or other therapeutic moieties for PSCA-targeted delivery to tumors. The engineered PSCA-specific antibodies can be coupled to nanosensors for detection (in vitro or in vivo) or nanoparticles for delivery (in vivo). One can also incorporate the PSCA antibody fragments into viral vectors for targeted gene therapy of tumors.

The invention addresses the unmet need for imaging of cancer, in early diagnosis or diagnosis of metastatic disease. In particular, there is a critical need for better agents for imaging prostate cancer for detection and staging. PSCA antibody fragment imaging will be very useful for imaging bone metastases and assessing response to treatment; there are no good imaging approaches currently available. Detection of pancreatic cancer is a critical need, and an imaging agent would be useful in high-risk patients. The invention describes high-affinity, highly specific engineered antibodies tailored for in vivo targeting and detection of PSCA in prostate cancer, bladder cancer, and pancreatic cancer patients.

Accordingly, in a first aspect, the invention provides high affinity PSCA antigen binding protein constructs which can be used in the treatment and detection of cancers which overexpress PSCA. In some embodiments, these constructs are minibodies, diabodies, triabodies, ScFv, or ScFv-Fc as described further below. In one embodiment, the invention provides an antigen binding protein construct directed toward a mammalian PSCA protein (e.g., human, murine) selected from the group consisting of a minibody, a diabody, and scFv-Fc wherein the selected construct has $V_L$ and $V_H$ domains that are substantially identical, respectively, to the $V_L$ domain and the $V_H$ domain of an anti-PSCA antibody. For example, the construct can be a minibody in which the $V_L$ and $V_H$ chain variable domains of the anti-PSCA antibody are fused to part of the hinge region of an antibody, an amino acid linker and the $C_H3$ domain of an immunoglobulin molecule. In other embodiments, the construct is a diabody.

In embodiments, where the construct is a minibody or diabody or scFV-Fc, the anti-PSCA antibody can be a humanized antibody and the $C_H3$ domain is from a human immunoglobulin molecule. In preferred embodiments, the anti-PSCA antibody is 2B3 or 1G8. In yet other embodiments, the construct is a minibody having $V_H$ and $V_L$ domains substantially identical to an scFv fragment designated herein as A11, A2, or C5. In still further embodiments, the construct has a $C_H3$ domain is from a human immunoglobulin molecule. For instance, the construct may have a hinge region and $C_H3$ domain are the human IgG hinge region and human $C_H3$ domain.

In some embodiments, the anti-PSCA antibody is a monoclonal antibody designated 1G8 (ATCC No. HB-12612), 2A2 (ATCC No. HB-1203), 2H9 (ATCC No. HB-12614), 3C5 (ATCC No. HB-12616), 3E6 (ATCC No. HB12618), 3G3 (ATCC No. HB-12615), or 4A10 (ATCC No. HB-12617).

The constructs according to the invention can also be linked to therapeutic agents or detectable markers. In some embodiments, the therapeutic agent is a cytotoxic agent. For instance, the agent can be ricin, ricin A-chain, doxorubicin, daunorubicin, TAXOL, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, arbrin A chain, modeccin A chain, alpha-sarcin, gelonin mitogellin, retstrictocin, phenomycin, enomycin, curicin, crotin, calicheamicin, sapaonaria officinalis inhibitor, maytansinoids, or glucocorticoidricin. In other embodiments, the therapeutic agent is a radioactive isotope. The radioactive isotope can be selected, for instance, from the group consisting of $^{212}Bi$, $^{131}I$, $^{111}In$, $^{90}Y$ and $^{186}Re$. In other embodiments the construct is linked to an anti-cancer pro-drug activating enzyme capable of converting a pro-drug to its active form.

In another preferred embodiments of the above, the PSCA targeted by the anti-PSCA antibody is human PSCA.

In another aspect, the invention provides an antigen binding protein construct selected from the group consisting of a minibody, a diabody, scFv and scFv-Fc wherein the selected construct has $V_L$ and $V_H$ domains that are substantially identical to the $V_L$ and $V_H$ domains of 2B3 or an scFv variant designated herein as A11, A2, or C5. In other embodiments, the binding constructs of the present invention may comprise one or more mutations found in the variant antibodies A11, A2, or C5.

In yet another aspect, the present invention provides an antigen binding protein construct selected from the group consisting of a minibody, a diabody, scFv and scFv-Fc wherein the selected construct comprises CDR regions of an anti-PSCA antibody. In certain embodiments, the anti-PSCA antibody will bind to PSCA with an affinity equal to or greater than the antibody designated 2B3. In other embodiments, the anti-PSCA antibody may be an affinity matured antibody, wherein the affinity matured antibody comprises a higher affinity for PSCA than does the parental antibody.

In another aspect, the anti-PSCA construct according to the invention is labeled with a detectable marker. The marker can be for instance, a radioisotope, a fluorescent compound, a bioluminescent compound, chemiluminescent compound, a metal chelator or an enzyme. Many radionuclides may be used as imaging labels, including without limitation, $^{124}I$, $^{86}Y$, $^{18}F$, $^{94}Tc$, and the like. One of skill in the art will know of other radionuclides particularly well suited for use in the present invention.

In further other embodiments of any of the above, the invention provides a pharmaceutical composition of the constructs according to the invention.

In another aspect still, the invention provides methods for treating a subject having cancer (e.g, prostate, pancreatic or bladder cancer), or inhibiting the growth of a prostate cancer cell expressing a Prostate Stem Cell Antigen (PSCA) protein comprising contacting the cancer cell (e.g., prostate, bladder, pancreatic cancer cell, with a construct according to the invention in an amount effective to inhibit the growth of the cancer cell. The method can kill the cancer cell. In some embodiments, the construct recognizes and binds the PSCA protein as shown below beginning with leucine at amino acid position 22 and ending with alanine at amino acid position 99. In additional embodiments, the method further comprises administering to a chemotherapeutic drug, radiation therapy. In some embodiments, the subject is also treated with hormone ablation therapy or hormone antagonist therapy.

The treatments may be given to the patient or subject by intravenously, intraperitoneally, intramuscularly, intratumorally, or intradermally. In some embodiments, the contacting comprises administering the construct directly into a prostate cancer, a bladder cancer, a pancreatic cancer or a metastasis thereof.

In another aspect, the invention provides methods of detecting a cancerous cell in a subject by contacting the cancer cell with a construct which bears a detectable marker. The methods can be used in screening patients at increased risk of cancer or to monitory response to therapy or to develop a prognosis for the cancer (e.g., prostate, bladder, or pancreatic cancers. The methods are particularly advantageous in detecting metastases of the cancer.

BRIEF DESCRIPTION OF THE DRAWINGS

FIG. 2: Comparison of 2B3 ScFv variant protein sequences. The $V_L$ sequence and part of the linker are in the top frame, the rest of the linker and $V_H$ sequences are in the lower frame. Also indicated are the CDRs: underlined wild type sequence. The mutations are highlighted in different shading. The parental ScFv P-2B3 sequence (SEQ ID NO:4) and variant C5 (SEQ ID NO:5), A2 (SEQ ID NO:6), and A11 (SEQ ID NO:7) ScFv sequences are shown.

FIG. 3: DNA sequence (SEQ ID NO:8) and translated protein sequence of the parental 2B3 minibody (SEQ ID NO:9). Also indicated are the starting points of the following protein segments: signal peptide (for mammalian secretion), light chain variable region ($V_L$), the 15 amino acid interdomain peptide linker, heavy chain variable region ($V_H$), human IgG1 hinge sequence and 10 amino acid extension, and the human IgG1 CHj domain followed by two stop codons.

FIG. 4: SDS-PAGE analysis of the four minibodies in non-reducing conditions: parental (p), A11, A2 and C5. The arrow indicates the expected molecular weight of a minibody.

FIG. 8: Biodistribution and microPET Imaging ranking of the 2B3 minibody variants. Biodistribution unit is a % ID/g values of weighed tissues in y-counter after 21 or 25 hours injection time. MicroPET Imaging values were obtained on the average values of 4 ROIs as shown in FIG. 6 and described in the materials and methods.

FIG. 10: Depictions of various constructs according to the invention.

FIG. 11: Schema for producing 2B3 variants.

FIG. 15: MicroPET imaging and biodistribution data for pancreatic cancer MIA PaCa-2 xenographic mice using parental 2B3 and variant A11 anti-PSCA minibodies.

Figure 16A:
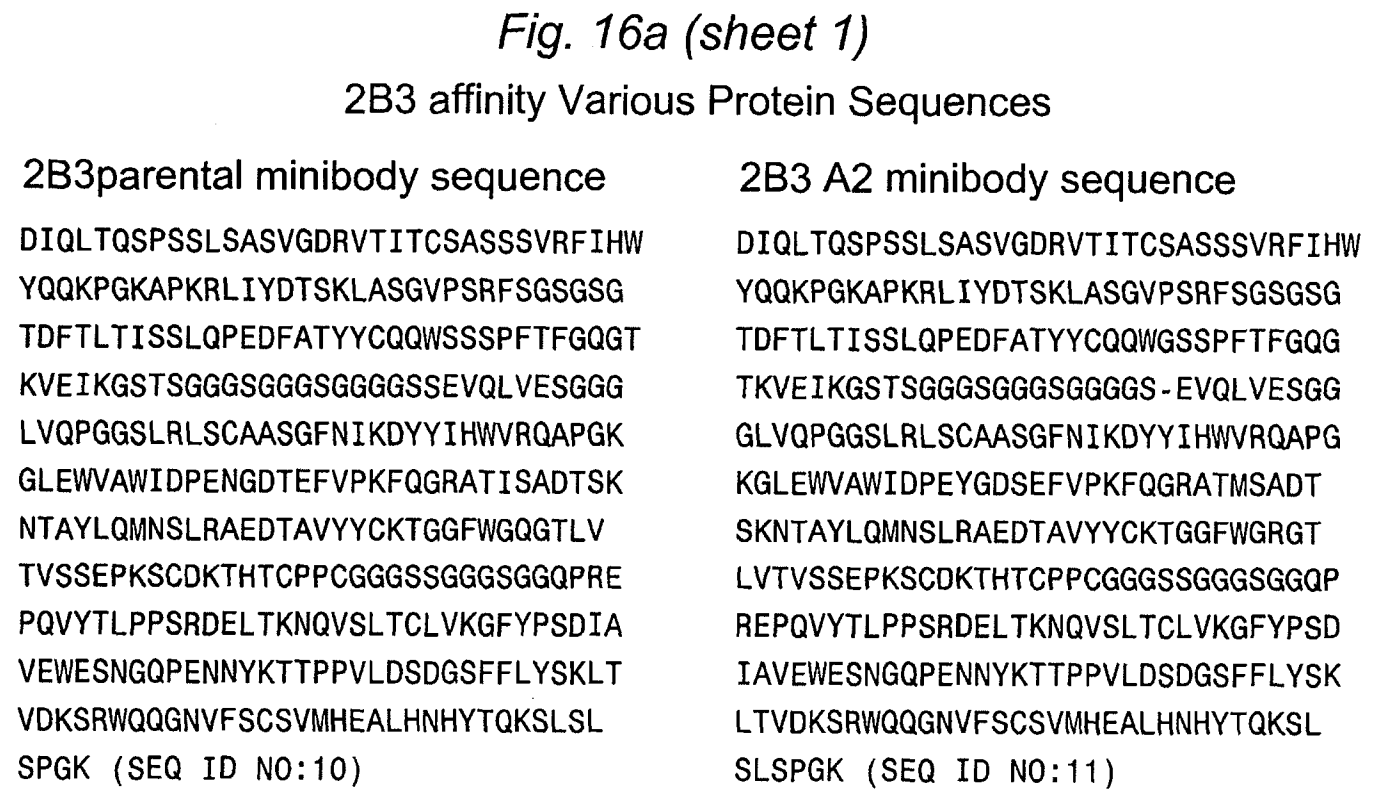

FIG. 16: Amino acid sequences of parental 2B3 (SEQ ID NO: 10) and variant A2 (SEQ ID NO:11), A11 (SEQ ID NO:12), and C5 (SEQ ID NO:13) anti-PSCA minibodies.

DETAILED DESCRIPTION OF THE INVENTION

Figure 1:
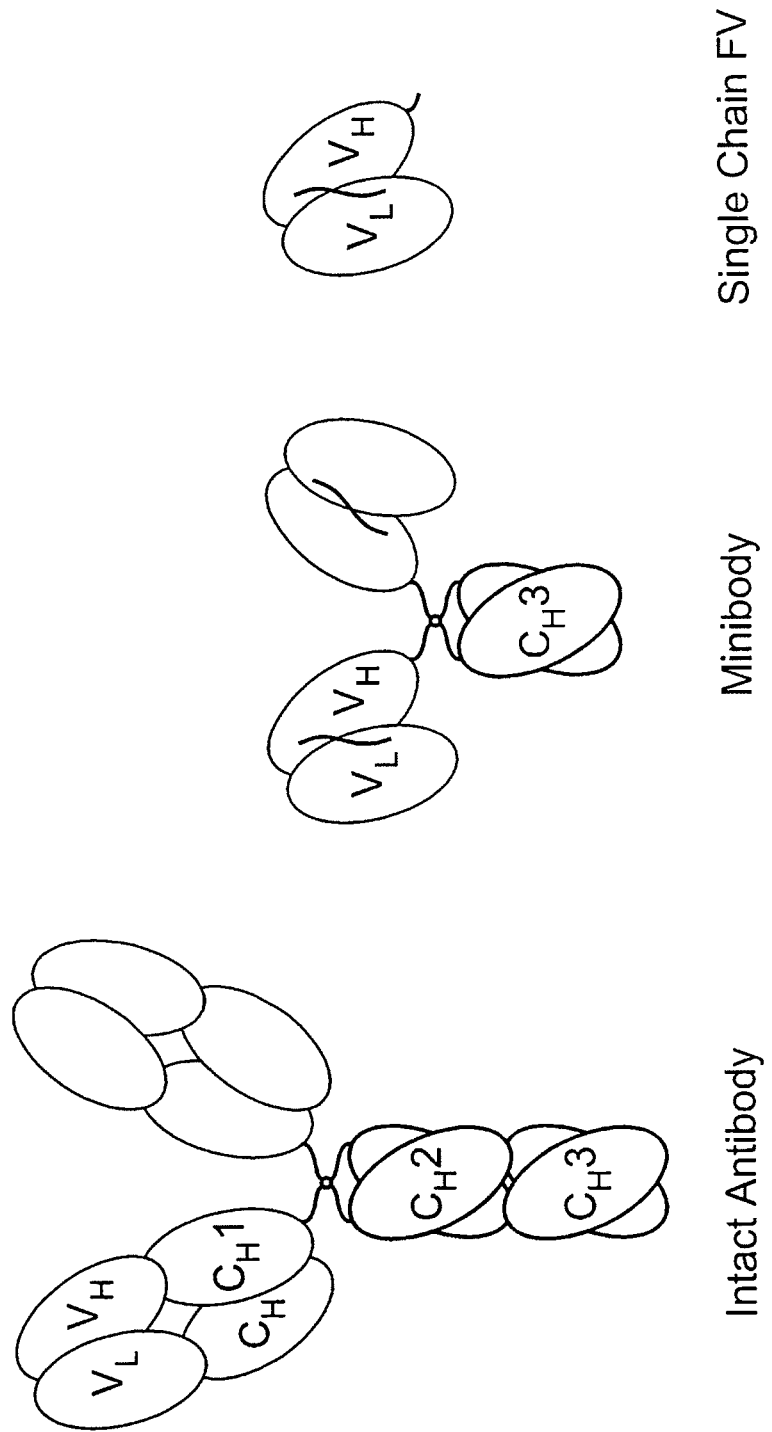
FIG. 1: Schematic overview of anti-PSCA minibody. A gene encoding the minibody is assembled in the order $V_L$-linker-$V_H$-hinge-$C_H3$, with the hinge and $C_H3$ domains derived from human IgG1. The protein self assembles into 80-kDa dimers.

Prolonged clearance kinetics have hampered the development of intact antibodies as imaging and therapeutic agents, despite their ability to effectively deliver radionuclides to tumor targets in vivo. Here, we also report genetically engineered antibody fragments which display rapid, high-level tumor uptake coupled with rapid clearance from the circulation in a nude mouse model to allow ready detection of tumors in vivo The 2B3 antibody was humanized by grafting on a human framework (Trastuzumab) and named (Olafsen T, et al. J. Immunotherapy 2007; 30:396; which is incorporated by reference in its entirety with respect to the description, biological activity, and making of the antibody). Antibody fragments of 2B3 have been generated for PET imaging application. One of these antibody fragments, the 2B3 minibody has demonstrated rapid and specific localization to PSCA-expressing tumors in a murine model. However, humanization has decreased the affinity of the intact antibody for PSCA from a Kd of 2.6 nM to 16.7 n M. In addition, reformatting of intact antibody into antibody fragments can also affect the binding efficiency. It has been shown that quantitative tumor retention of ScFvs increases with affinity but only to a threshold close to $10^{-9}$M (Adams G P, et al. Cancer Res. 2001; 61:4750). There are no published data on the effect of minibody affinity on tumor targeting and imaging properties. Here, we describe the generation of three high affinity anti-PSCA ScFvs, and the subsequent generation and characterization of three high affinity anti-PSCA minibodies. We generated minibody fragments with better tumor targeting/imaging aptitude. In some embodiments, with the regard to the constructs of the invention, there is a proviso that the construct comprises a $V_H$ or $V_L$ domain that is not identical to a corresponding domain or the 2B3 antibody.

In one embodiment, the present invention provides antigen binding constructs selected from the group consisting of an antibody, a minibody, a diabody, an scFv, an scFv-Fc, and the like, wherein the $V_L$ and $V_H$ domains are substantially identical to those found in 2B3. In a second embodiment, the antigen binding construct may comprise one or more mutations found in an antibody variant designated herein as A11, A2, or C5. In a third embodiment, the binding construct comprises at least one mutation at a residue corresponding to an amino acid of SEQ ID NO:4 selected from the group consisting of T5, S10, V15, S91, S123, S131, N179, T182, I194, A203, G213, Q228, and a combination thereof. In certain embodiments, the at least one mutation comprises a mutation corresponding to a mutation in SEQ ID NO:4 selected from the group comprising T5I, S10I, V15M, S91G, Δ123, S131Y, N179Y, T182S, I194M, A203V, E213K, Q228R, and a combination thereof. In other embodiments, the binding constructs of the invention comprise mutations corresponding to those found in variants A11, A2, or C5.

In a certain embodiment, the present invention provides a minibody wherein the $V_L$ and $V_H$ domains are substantially identical to those found in SEQ ID NO:10. In one embodiment, a minibody of the present invention comprises an amino acid sequence of SEQ ID NO:10. In other embodiments, the minibody comprises an amino acid sequence that is substantially identical to SEQ ID NO:10, wherein said minibody binds to PSCA with a higher affinity than a minibody of SEQ ID NO:10. In yet other embodiments, the minibody may comprise one or more mutations at a residue corresponding to an amino acid of SEQ ID NO:10 selected from the group comprising T5, S10, V15, S91, S123, S131, N179, T182, I194, A203, G213, Q228, and a combination thereof. In yet another embodiment, the construct may comprise a sequence selected from SEQ ID NOS:11, 12, and 13.

In one embodiment, the invention provides an antigen binding protein construct selected from the group consisting of a minibody, a diabody, scFv and scFv-Fc wherein the selected construct comprises CDR regions of an anti-PSCA antibody. In one embodiment, the binding protein construct will comprise at least one CDR region selected from a CDR-L1, CDR-L2, CDR-L3, CDR-H1, CDR-H2, or CDR-H3 from an anti-PSCA antibody. In yet other embodiments, the protein binding construct may comprise all 3 light chain CDR regions or all three heavy chain CDR regions. In one embodiment, the protein binding constructs of the present invention may comprise all of the CDR regions of an anti-PSCA antibody. In certain embodiments, the anti-PSCA antibody will bind to PSCA with an affinity equal to or greater than the antibody designated 2B3. In other embodiments, the anti-PSCA antibody may be an affinity matured antibody, wherein the affinity matured antibody comprises a higher affinity for PSCA than does the parental antibody. In particular embodiments, the parental anti-PSCA antibody may be selected from the group consisting of 1G8 (ATCC No. HB-12612), 2A2 (ATCC No. HB-1203), 2H9 (ATCC No. HB-12614), 3C5 (ATCC No. HB-12616), 3E6 (ATCC No. HB12618), 3G3 (ATCC No. HB-12615), 4A10 (ATCC No. HB-12617), and 2B3. In other embodiments, the CDRs may be selected from those found in SEQ ID NOS:10, 11, 12, and 13.

A "minibody" is an engineered antibody construct comprised of the variable heavy (VH) and variable light (VL) chain domains of a native antibody fused to the hinge region and to the CH3 domain of the immunoglobulin molecule (see, FIG. 1). Minibodies are thus small versions of whole antibodies encoded in a single protein chain which retain the antigen binding region, and the CH3 domain which to permit assembly into a bivalent molecule and the antibody hinge to accommodate dimerization by disulfide linkages. In contrast, native antibodies are comprised of four chains, two heavy and two light. The size, valency and affinity of the minibody is particularly suited for in vivo targeting. Expression in bacterial or mammalian cells is simplified because minibodies can be produced as single amino acid chains (see, U.S. Pat. No. 5,837,821) which is incorporated by reference herein in its entirety and particularly with reference to minibodies, their structure, ways of making them, and their suitable pharmaceutical formulations.

A "diabody" comprises a first polypeptide chain which comprises a heavy (VH) chain variable domain connected to a light chain variable domain (VL) on the first polypeptide chain (VH-VL) connected by a peptide linker that is too short to allow pairing between the two domains on the first polypeptide chain and a second polypeptide chain comprising a light chain variable domain (VL) linked to a heavy chain variable domain VH on the second polypeptide chain (VL-VH) connected by a peptide linker that is too short to allow pairing between the two domains on the second polypeptide chain. The short linkages force chain pairing between the complementary domains of the first and the second polypeptide chains and promotes the assembly of a dimeric molecule with two functional antigen binding sites.

To construct bispecific diabodies the V-domains of different antibodies (e.g., antibody A and antibody B) are fused to create the two chains (e.g., VHA-VLB, VHB-VLA). Each chain is inactive in binding to antigen, but recreates the functional antigen binding sites of antibodies A and B on pairing with the other chain.

PSCA and its expression in cancer of the prostate, bladder, and pancreas is disclosed in U.S. Pat. No. 6,756,036 which is incorporated by reference in its entirety. The human PSCA translated amino acid sequence is:

```
                                          (SEQ ID NO: 1)
MKAVLLALLMAGLALQPGTALLCYSCKAQVSNEDCLQV

ENCTQLGEQCWTARIRAVGLLTVISKGCSLNCVDDS

QDYYVGKKNITCCDTDLCNASGAHALQPAAAILALLPAL

GLLLWGPGQL
```

The terms "substantially identical" in the context of two or more nucleic acids or polypeptide sequences, refer to two or more sequences or subsequences that are the same or have a specified percentage of amino acid residues or nucleotides that are the same (i.e., about 80% identity, preferably at least 65%, 70%, 75%, 80%, 85%, 90%, 91%, 92%, 93%, 94%, 95%, 96%, 97%, 98%, 99%, or higher identity) over the referenced sequences or portions, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). The definition also includes sequences that have deletions and/or additions, as well as those that have substitutions. Preferably, the sequence identity is at least 85%, 90%, 95% 97% between two referenced domains. In some embodiments, the difference in sequence is just by one, two, three or four, or from five to 12, amino acids as to referenced sequence or domain. As described below, the preferred algorithms can account for gaps and the like. Preferably, identity exists over a region that is at least about 15 amino acids or nucleotides in length, or more preferably over a region that is 15-50 amino acids or nucleotides in length. In other embodiments, the identity may exist over a region that is at least about 50, 100, 150, 200, or more amino acids.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected over a specified range of residues (e.g., 20 to 50, usually about 50 to about 200, more usually about 100 to about 150) in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms capply to amino acid polymers in which one or more amino acid residue is an artificial chemical mimetic of a corresponding naturally occurring amino acid, as well as to naturally occurring amino acid polymers and non-naturally occurring amino acid polymer.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" or "detectable marker" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of suitable antibodies or constructs of the invention and for use according to the invention, e.g., recombinant, monoclonal, or polyclonal antibodies, many techniques known in the art can be used (see, U.S. Patent Application Publication No. 20070196274 and U.S. Patent Application Publication No. 20050163782, which are each incorporated by reference in their entireties, particularly with respect to minibody and diabody design) (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, Antibodies, A Laboratory Manual (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

The antibodies of the invention include derivatives that are modified, i.e., by the covalent attachment of any type of molecule to the antibody. For example, the antibody derivatives include, without limitation, antibodies that have been modified by glycosylation, acetylation, pegylation, phosphorylation, amidation, derivatization by known protecting/blocking groups, proteolytic cleavage, linkage to a cellular ligand or other protein, and the like. Any of numerous chemical modifications may be carried out by known techniques, including, but not limited to specific chemical cleavage, acetylation, formylation, metabolic synthesis of tunicamycin, etc. Additionally, the derivative may contain one or more non-natural amino acids.

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332: 323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

In some embodiments, the antibody is conjugated to an "effector" moiety. The effector moiety can be any number of molecules, including labeling moieties such as radioactive labels or fluorescent labels, or can be a therapeutic moiety. In one aspect the effector moieties modulates the activity of the protein. Such effector moieties include, but are not limited to, an anti-tumor drug, a toxin, a radioactive agent, a cytokine, a second antibody or an enzyme. Further, the invention provides an embodiment wherein the antibody of the invention is linked to an enzyme that converts a prodrug into a cytotoxic agent.

The immunoconjugate can be used for targeting the effector moiety to a PSCA-positive cell, particularly cells, which overexpress the PSCA protein. Such differences can be readily apparent when viewing the bands of gels with approximately similarly loaded with test and controls samples. Examples of cytotoxic agents include, but are not limited to ricin, doxorubicin, daunorubicin, TAXOL, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

In some embodiments, the invention provides antigen binding protein constructs used to systemically to treat cancer (e.g., prostate, pancreatic or bladder cancer) alone or when conjugated with an effector moiety. PSCA-targeting constructs conjugated with toxic agents, such as ricin, as well as unconjugated antibodies can be useful therapeutic agents naturally targeted to PSCA bearing cancer cells. Such constructs can be useful in blocking invasiveness Additionally, the antigen-binding protein constructs of the invention can be used to treat cancer. In such a situation, the construct is joined to at least a functionally active portion of a second protein or toxic molecule having therapeutic activity. The second protein can include, but is not limited to, an enzyme, lymphokine, oncostatin or toxin. Suitable toxins include doxorubicin, daunorubicin, TAXOL, ethiduim bromide, mitomycin, etoposide, tenoposide, vincristine, vinblastine, colchicine, dihydroxy anthracin dione, actinomycin D, diphteria toxin, Pseudomonas exotoxin (PE) A, PE40, ricin, abrin, glucocorticoid and radioisotopes.

Techniques for conjugating therapeutic agents to constructs according to the invention are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide or construct according to the invention, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires a construct be selected for its specificity for a particular protein. A variety of immunoassay formats may be used to select constructs specifically immunoreactive with PSCA. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

By "therapeutically effective dose or amount" herein is meant a dose that produces effects for which it is administered. The exact dose and formulation will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Remington: *The Science and Practice of Pharmacy,* 20th Edition, Gennaro, Editor (2003), and Pickar, *Dosage Calculations* (1999)).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The methods find particular application in the diagnosis, prognosis and treatment of cancers which overexpress PSCA, for example, prostate, pancreatic and bladder cancers. In certain embodiments the methods are applied to hormone refractory or therapy resistant cancers. In certain embodiments the methods are applied to metastatic cancers.

Treatment will generally involve the repeated administration of the constructs and their immunoconjugates via an acceptable route of administration such as intravenous injection (IV), at an effective dose. Dosages will depend upon various factors generally appreciated by those of skill in the art, including without limitation the type of cancer and the severity, grade, or stage of the cancer, the binding affinity and half life of the agents used, the desired steady-state antibody concentration level, frequency of treatment, and the influence of chemotherapeutic agents used in combination with the treatment method of the invention. Typical daily doses may range from about 0.1 to 100 mg/kg. Doses in the range of 10-500 mg of the constructs or their immunoconjugates per week may be effective and well tolerated, although even higher weekly doses may be appropriate and/or well tolerated. The principal determining factor in defining the appropriate dose is the amount of a particular agent necessary to be therapeutically effective in a particular context. Repeated administrations may be required in order to achieve tumor inhibition or regression. Initial loading doses may be higher. The initial loading dose may be administered as an infusion. Periodic maintenance doses may be administered similarly, provided the initial dose is well tolerated.

Direct administration of the constructs is also possible and may have advantages in certain contexts. For example, for the treatment of bladder carcinoma, the agents may be injected directly into the bladder.

In another embodiment, the invention provides polynucleotides comprising a nucleotide sequence encoding an antibody of the invention and fragments thereof. In one embodiment, the present invention provides an expression vector encoding for an antibody or fragment thereof of the present invention. In another embodiment, the present invention provides polynucleotides encoding an antibody of the present invention for use in gene therapy or in vivo administration.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Methods of Administration and Formulation

The constructs are administered to a subject in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration is preferred. The administration may be local or systemic.

The compositions for administration will commonly comprise an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the agent. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that constructs when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations, particularly, constructs and immunoconjugates and inhibitors for use with the present invention can be prepared by mixing a construct having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants. The construct can be formulated at a concentration of between 0.5-200 mg/ml, or between 10-50 mg/ml.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunocongugates may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, and the like.

In other embodiments, the methods of the invention may be practiced together with other cancer therapies (e.g., radical prostatectomy), radiation therapy (external beam or brachytherapy), hormone therapy (e.g., orchiectomy, LHRH-analog therapy to suppress testosterone production, anti-androgen therapy), or chemotherapy. Radical prostatectomy involves removal of the entire prostate gland plus some surrounding tissue. This treatment is used commonly when the cancer is thought not to have spread beyond the tissue. Radiation therapy is commonly used to treat prostate cancer that is still confined to the prostate gland, or has spread to nearby tissue. If the disease is more advanced, radiation may be used to reduce the size of the tumor. Hormone therapy is often used for patients whose prostate cancer has spread beyond the prostate or has recurred. The objective of hormone therapy is to lower levels of the male hormones, androgens and thereby cause the prostate cancer to shrink or grow more slowly. Luteinizing hormone-releasing hormone (LHRH) agonists decrease the production of testosterone. These agents may be injected either monthly or longer. Two such analogs are leuprolide and goserelin. Anti-androgens (e.g., flutamide, bicalutamide, and nilutamide) may also be used. Total androgen blockade refers to the use of anti-androgens in combination with orchiectomy or LHRH analogs, the s combination is called. Chemotherapy is an option for patients whose prostate cancer has spread outside of the prostate gland and for whom hormone therapy has failed. It is not expected to destroy all of the cancer cells, but it may slow tumor growth and reduce pain. Some of the chemotherapy drugs used in treating prostate cancer that has returned or continued to grow and spread after treatment with hormonal therapy include doxorubicin (Adriamycin), estramustine, etoposide, mitoxantrone, vinblastine, and paclitaxel. Two or more drugs are often given together to reduce the likelihood of the cancer cells becoming resistant to chemotherapy. Small cell carcinoma is a rare type of prostate cancer that is more likely to respond to chemotherapy than to hormonal therapy.

The combined administrations contemplates co-administration, using separate formulations or a single pharmaceutical formulation, and consecutive administration in either order, wherein preferably there is a time period while both (or all) active agents simultaneously exert their biological activities.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

Preferred pharmaceutical preparations deliver one or more constructs according to the invention, optionally in combination with one or more chemotherapeutic agents or immunotherapeutic agents, in a sustained release formulation. The construct may be administered therapeutically as a sensitizing agent that increases the susceptibility of tumor cells to other cytotoxic cancer therapies, including chemotherapy, radiation therapy, immunotherapy and hormonal therapy.

In therapeutic use for the treatment of cancer, the constructs utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The pharmaceutical preparations for use according to the invention are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

Methods of Tumor Imaging

In certain embodiments, the present invention provides methods of imaging cancer cells or tumors in vivo through administration of antibodies of the invention. In one embodiment, the present invention provides a method of imaging a cancer cell in vivo, the method comprising administering a labeled anti-PSCA antibody to a mammal and imaging the antibody in vivo. The methods of the present invention may be used to image a cancer cell in mammal, including without limitation, a mouse, rat, hamster, rabbit, pig, human, and the like.

Methods of in vivo imaging are well known in the art and include without limitation, magnetic resonance imaging (MRI), nuclear magnetic resonance (NMR) (R. Weissleder, 1999, Radiology 212:609-14), computerized axial tomography (CAT) scan, cooled charged coupled device (CCD) camera optical imaging (Honigman, et al., 2001 Mol. Ther. 4:239-249), bioluminescent optical imaging (P R Contag, et al., 1998 Nat. Med. 4:245-247), position emission tomography (PET) (M E Phelps, 1991 Neurochemical Research 16:929-994; J G Tjuvajev, et al., 1998 Cancer Res 58:4333-4341), single photon emission computed tomography (J G. Tjuvajev, et al., 1996 Cancer Res. 45:4087-4095), microPET (reviewed in McVeigh, 2006, Circ. Res. 98:879-86), and the like.

EXAMPLES

The following examples are offered to illustrate, but not limit, the claimed invention.

Example 1

This example describes the construction of a mutant scFv yeast display library and the selection of ScFv mutants with improved PSCA binding affinity.

Oligonucleotides and vectors used in the construction of the library include; Gap 5'-5'-TTAAGCTTCTGCAG-GCTAGTG-3' (SEQ ID NO:2); Gap 3': 5'-GAGACCGAG-GAGAGGGTTAGG-3' (SEQ ID NO:3); pYD2 inside the NcoI-Not1 restriction sites (Razai A, et al. J Mol Biol. 2005; 351:158).

2B3 ScFv gene was first cloned into the yeast display vector pYD2 (Razai A, et al. J. Mol. Biol. 2005; 351:158) using NcoI-Not1 restriction sites. A bacterial clone with the correct sequence was amplified and DNA extracted with QIAprep Spin Miniprep. Random mutations were introduced into the 2B3 Scfv gene using error prone PCR as follows: 2B3 ScFv gene was subject to 20 cycles of PCR with Taq in the presence of 100 mM $MnCl_2$ to generate random mutations. The PCR product was run on an agarose gel and purified using QIAquick gel extraction. The purified PCR product was re-amplified using a proof reading DNA polymerase for 35 cycles. Both PCRs were carried out with the Gap5' and Gap3' primers. The amplified 2B3 Fv gene was again run on an agarose gel and purified using QIAquick gel extraction. Mutated scFv genes and NcoI-Not1 digested pYD2 were used to transform LiAc-treated EBY 100 cells by gap repair. The resulting gene repertoire was cloned into pYD2 using gap repair to create a library of $5.9 \times 10^5$ transformants Transformation mixes were cultured and sub-cultured in SD-CAA. Library size was determined by plating serial dilutions of the transformation mixture on SD-CAA plates.

For selection, scFv display was induced by culturing in SG-CAA media plus zeocin for 24 hours at 20° C. For the first round of selection 20 million yeast (more than 30 times the library size) were washed and resuspended in FACS buffer (phosphate-buffered saline (pH 7.4), 0.5% bovine serum albumin) to which 200 nM of PSCA human Gamma 1 fusion protein was added and incubated for 1 hour at room temperature. The concentrations of PSCA human Gamma 1 used for round 2, 3 and 4 of sorting were 5 nM, 2 nM and 1 nM respectively. Cells were incubated for 30 minutes with secondary antibodies at 4° C., washed once with FACS buffer, resuspended in 200-500 µl of FACS buffer and sorted on a FACSAria. Typically 1% of the PSCA binding population was gated for collection. Collected cells were grown in SD-CAA media and used for the next round of sorting after induction in SG-CAA. Twenty yeast clones from the fourth round of sorting were analyzed by flow cytometry. Eight of these clones showing strong staining were selected (A2, A4, A8, A9, A11, A12, B5 and C5) and their DNA sequenced. A2, A4, A8, A9, A12, B5 protein sequences were identical with 10 mutations, A11 had 6 mutations and C5 had 4 mutations. Protein sequence comparisons of the parental 2B3 ScFv with A2, A11 and C5 are shown in FIG. 2.

Example 2

This example describes the reformatting of mutant 2B3 scFv's into minibodies.

The parental 2B3 minibody pEE12 construct (FIG. 2) was used as a backbone to generate the three 2B3 minibody affinity variants where the wild type ScFv insert was replaced by each of the three 2B3 ScFv affinity variants. The parental 2B3 minibody construct is presented in FIG. 1. Briefly, $V_L$ and $V_H$ regions were fused with a 15 residue long Gly-Ser rich linker in the $V_L$-$V_H$ orientation. This ScFv is flanked by a signal peptide upstream and the human IgG1$C_H$3 domain via the human IgG1 hinge including a 10 residue GlySer peptide linker downstream. The final product was cloned into the PEE 12 vector of expression (Lonza Biologics, Slough, UK). This vector contains the hCMV promoter and the glutamine synthetase gene for selection (Bebbington et al., *Biotechnology* (N Y). 1992; 10: 169). The parental 2B3 minibody pEE12 construct was used as a backbone to generate the three 2B3 minibody affinity variants. The parental pEE12 DNA was digested with Xba I and Xho I restriction sites to remove the parental 2B3 ScFv insert that was replaced by each of the three 2B3 ScFv affinity variants. Xba I-Xho I restriction sites were added at the extremities of 2B3 ScFv affinity variants for sub-cloning in pEE12, by extension PCR.

Example 3

This example describes the expression, selection, and purification of anti-PSCA minibodies.

A total of $2 \times 10^6$ NS0 mouse myeloma cells were transfected with 10 ug of linearized (cut with SalI) vector DNA by electroporation and selected in glutamine-deficient media as described (Yazaki P J, et al. J Immunol Methods. 2001; 253: 195). Clones were screened for expression by ELISA, whereby the desired protein was captured by goat anti-human IgG (Fc specific) and detected by alkaline phosphastase (AP)-conjugated goat anti-human IgG (Fc specific) (both from Jackson ImmunoResearch Labs, West Grove, Pa.). The highest producing clones were expanded and brought to terminal culture.

Figure 4:
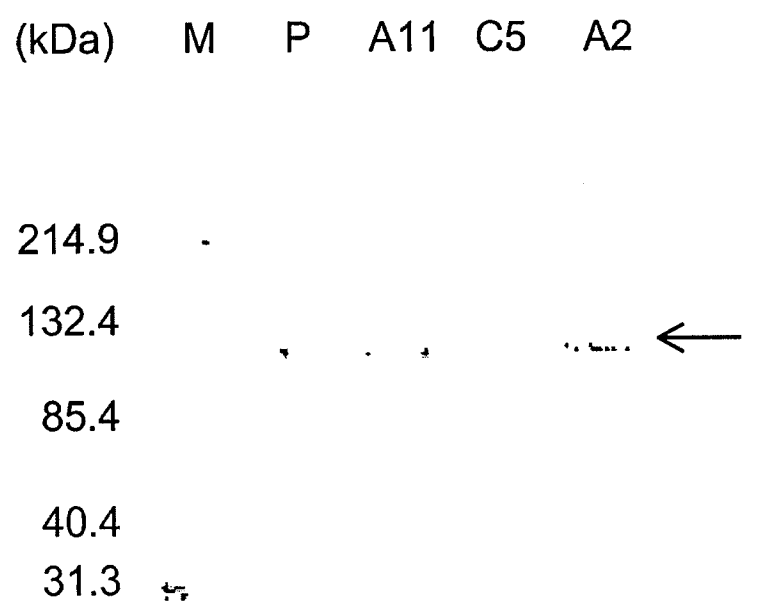

Soluble minibodies were purified from cell culture supernatants by Protein L chromatography using a Thermal Separations Products HPLC with an in-line UV monitor, equipped with a preparative Poros 50 A column (Applied Biosystems, Foster City, Calif.) and analyzed on SDS-PAGE (FIG. 3). The four minibodies showed similar results. All the minibodies migrated as molecular weight species of ~95 kDa under non-reducing conditions and all showed good purity. In addition, the A11 minibody eluted at 29.5 minutes as expected when run on a calibrated size exclusion column (FIG. 4). Supernatants were loaded onto a 10×50 mm column and eluted using 0.1 M glycine pH 2.5, the pH was immediately neutralized with 2M Tris-HCl pH 8. The purified proteins were then dialyzed against PBS using a molecular porous membrane tubing (mwco: 30,000) and concentrated with a Vivascience Vivaspin 20 (mwco: 30,000). Final protein concentrations were determined by measuring UV absorbance at 280 nm, using the parental murine antibody as the standard.

Example 4

This example describes the biochemical characterization of anti-PSCA minibodies.

Size and composition: Purified proteins were analyzed by SDS-PAGE (FIG. 3) under non-reducing conditions. Native structural size was determined by size exclusion columns (Superdex 75) (Pharmacia).

Figure 5:
FIG. 5: Size-exclusion HPLC of A11 minibody showing homogenous peak at expected molecular size.

The ranking of the four minibodies was determined by competition ELISA and flow cytometry (FIG. 5). The relative affinity as measured by competition ELISA indicated that all three affinity variants had higher affinity than the parental, with an improvement of 4.4×, 3.0× and 1.9× for A2, A11 and C5 respectively compared to the parental. Flow cytometry data also resulted in ranking the four minibodies in the same order when targeting PSCA expressed at the cell surface. In conclusion, the affinity ranking of the four minibodies was: A2>A11>C5>parental.

Competition ELISA: PSCA relative binding affinity for the minibodies was determined by competition ELISA in which microtiter plate wells were coated with purified PSCA-Fc (Olafsen T, et al. J. Immunotherapy 2007: 30:396).

Flow Cytometry: was conducted to assess cellular PSCA binding activity. An EBV transformed B-cell lymphoma cell line stably transfected with PSCA were used. Briefly, cells $5 \times 10'$ were incubated for 30 min on ice with 100 µl of minibody at 2 ug/ml concentration. Cells were washed and stained with goat anti-hFc PE conjugated antibody at 1:100 dilution.

Radioiodination: Purified minibodies were radioiodinated with the positron emitting isotope $^{124}$I (sodium iodide in 0.02 M NaOH; radionuclide purity >99%) provided by Advanced Nuclide Technologies, Indianapolis, Ind. as previously described (Kenanova, Olafsen et al., Cancer Res. 65:622, 2005). Immunoreactivity was assayed by incubating radioiodinated-minibody with an excess amount of SKW-PSCA$^+$ cells for an hour at room temperature, centrifugating the cells, and counting radioactivity present into the supernatant compared to the control.

Example 5

This example describes MicroPET imaging and biodistribution studies of anti-PSCA minibodies.

Figure 6A:
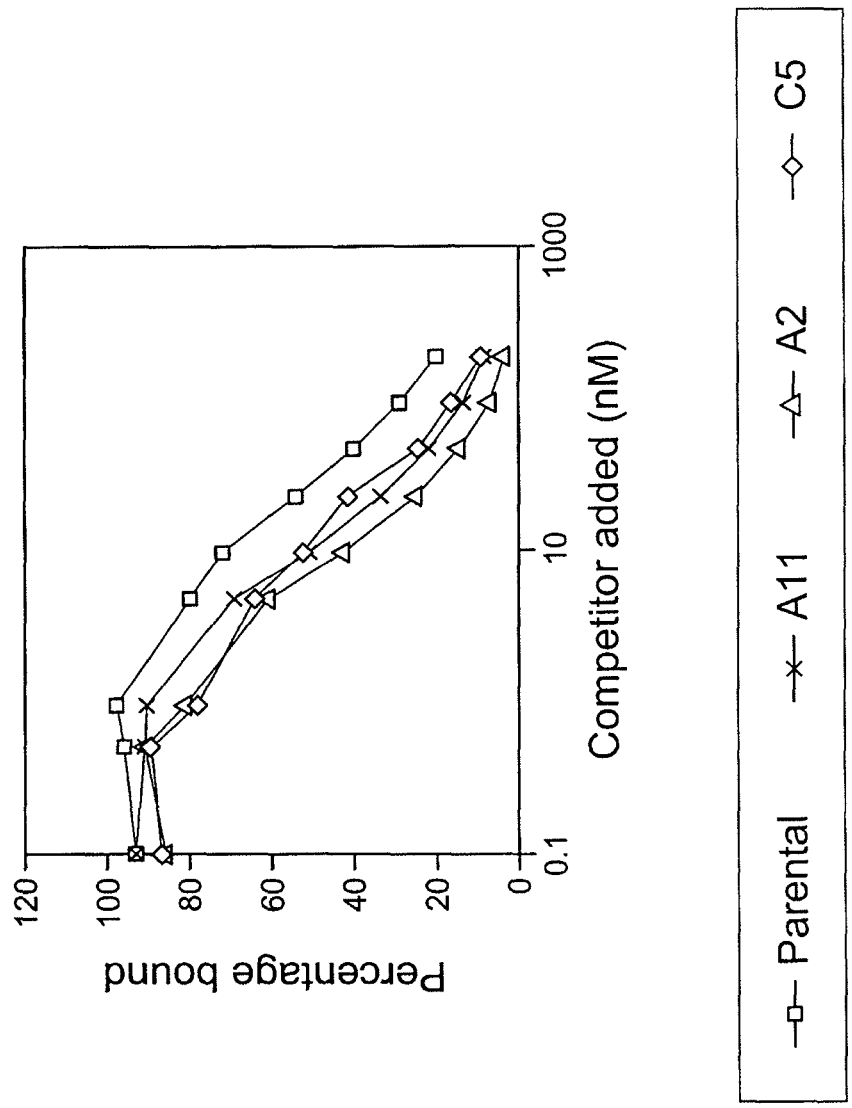
FIG. 6: Affinity ranking. (A) by Competitive ELISA binding assay: Plates were coated with CEA and biotinylated intact, chimeric anti-CEA antibody was used as probe. (B) by flow cytometry: 5 pg/ml of each minibody was incubated with PSCA expressing cells. Cells were then stained with anti Human Fc PE conjugated.

All animal studies were conducted under protocols approved by the Chancellor's Animal Research Committee at the University of California, Los Angeles. Xenografts were established in 7- to 8-week-old male nude mice (Charles River Laboratories, Wilmington, Mass.) by s.c. inoculation of $2 \times 10^6$ LAPCP AD cells in the shoulder region. After 14 days, when tumor masses were in the range of 100 to 300 mg, 100 µCi of isotope $^{124}$I (30-50 µg protein) was injected into the tail vein of each animal. Mice were imaged using a P4 microPET scanner (Concorde Microsystems, Inc., Knoxville, Tenn.). To enable imaging, mice were anesthetized using 2% isoflurane, positioned in a prone position along the long axis of the microPET scanner and imaged. Acquisition time was 10 minutes (1 bed position), and images were reconstructed using a filtered backprojection reconstruction algorithm. Images were displayed and regions of interest (ROI) were drawn as described in FIG. 6 and quantified using AMIDE (Loening and Gambhir, Molecular Imaging 2: 131, 2003). After scanning, tumors, liver, spleen, kidney, lung, and blood were excised, weighed and counted in a well counter (Cobra II AutoGamma, Packard, Ill.). Background, crossover, and decay corrections were done. Results were calculated as percentage of injected dose per gram of tissue (% ID/g).

Figure 7:
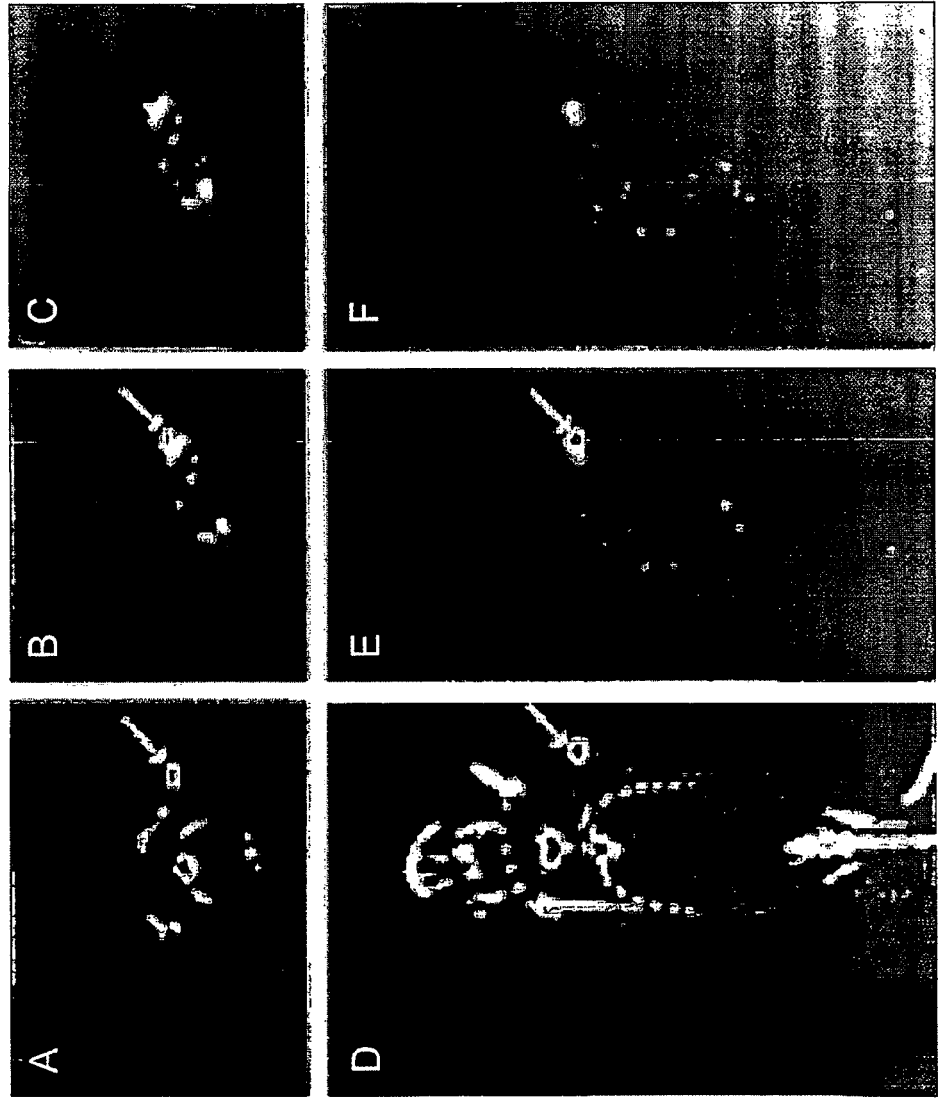
FIG. 7: Co-registered microPET/microCT scan of a nude mouse bearing LAPC-9AD (PSCA-positive human prostate cancer) xenografts. The mouse was injected with 1-1 24 radiolabeled A11 minibody variant and scanned serially. A, B, C; saggital sections; D, E, F; coronal sections. A, D; coregistered microPET and microCT, showing ROI (region of interest) as a white rectangle. B, E; microPET images and ROI C, F; microPET images only.
Figure 9:
FIG. 9: Summary of PSCA data and properties.
Figure 12:
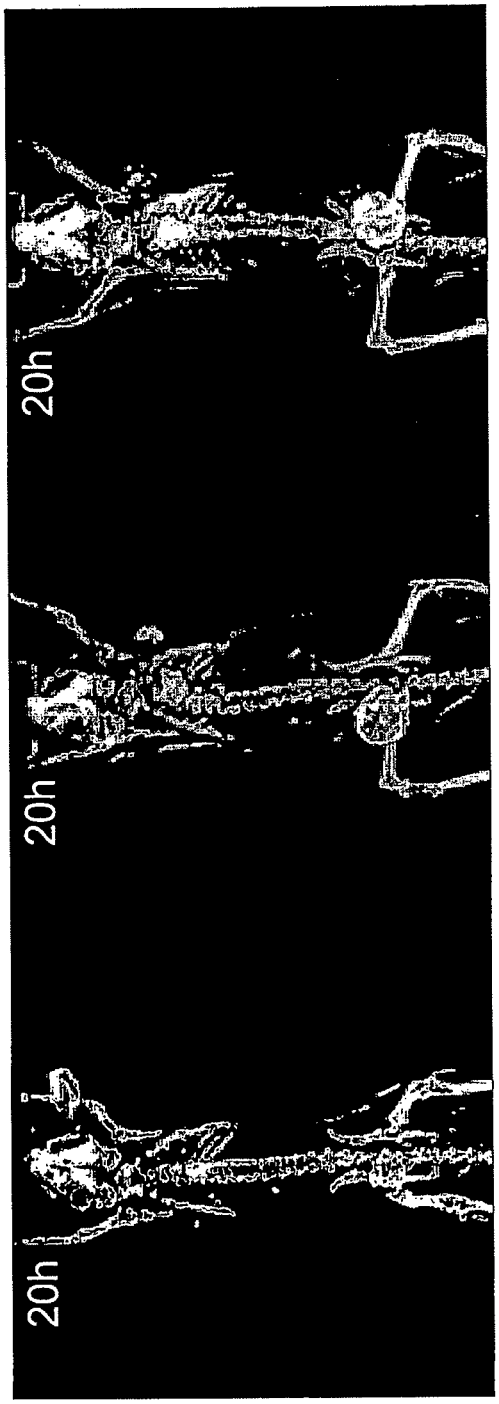
FIG. 12: MicroPET imaging and biodistribution data for various constructs.
Figure 13:
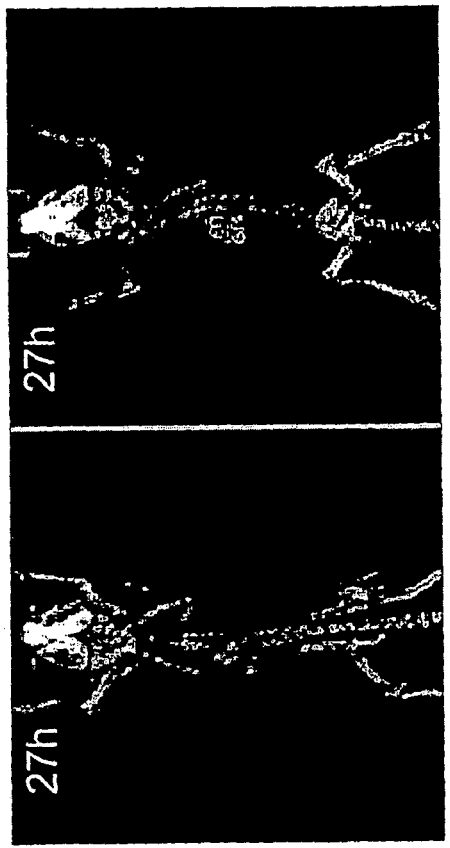
FIG. 13: MicroPET imaging and biodistribution results for A11 and parent 2B3.

To evaluate tumor targeting and microPET imaging efficiency, $^{124}$I-labeled minibodies were injected into Nude mice bearing LAPC-9AD tumors on the right shoulder. Whole-body micoPET and CT scans were performed at 21 h and/or 25 h, after which the animals were sacrificed, and activity in various tissues quantified using a gamma counter. To quantify microPET imaging, four 3-dimentional ROIs were drawn in the tumors and four other ROI in soft tissues around the tumor as presented in FIG. 6. The ROI position and size were based on CT image information. Both biodistribution and imaging quantification are presented as a ratio of tumor signal to background. A11 minibody gave the best biodistribution and imaging data in an experiment that compared the three affinity variant (FIG. 7A). Thus the affinity ranking (FIG. 5) and in vivo tumor targeting/imaging ranking (FIG. 7A) of the three affinity variant minibodies are different, suggesting that in our model in vivo tumor targeting/imaging effectiveness is not solely dependant on the inherent affinity of the tracer to its target. A2 which has the best affinity to PSCA did not give the best in vivo tumor targeting/imaging results. One possible explanation for this discordance is that A2 has a substitution of an asparagine into a tyrosine in $V_L$ CDR2, and that iodination of this new tyrosine could affect the binding to PSCA. In a second experiment A11 minibody was compared to the parental minibody for their in vivo tumor targeting/imaging effectiveness. A11 showed a 20% increase in tumor targeting (n=3) and a 141% increase in microPET tumor imaging (n=2) (FIG. 7B).

Example 6

This example describes the imaging of various pancreatic cancer tumors using anti-PSCA minibodies.

In order to evaluate the targeting and imaging potential of affinity matured anti-PSCA minibodies, $^{124}$I-labeled minibodies (parental 2B3 and variant A11) were injected into athymic nude mice bearing tumors that express low levels of target PSCA antigen. Briefly, xenographic mice bearing either human Capan-1 (FIG. 14) or human MIA PaCa-2 (FIG. 15) pancreatic tumors were injected with either 200 or 300 μg of labeled anti-PSCA minibody. Wholebody micoPET and CT scans were performed as before, and tissue radioactivity was determined. Similarly, quantification of microPET imaging and ROI position and size were determined as in example 5.

Figure 14:
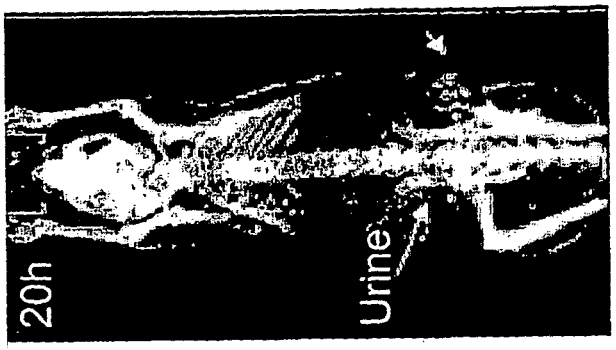
FIG. 14: MicroPET imaging and biodistribution data for pancreatic cancer Capan-1 xenographic mice using parental 2B3 and variant A11 anti-PSCA minibodies.

As can be seen in FIGS. 14 and 15, variant A11 anti-PSCA microbodies consistently demonstrated improved tumor to muscle specificity ratios as compared to parental 2B3 minibodies. The nearly 2-fold enhancement in in vivo specificity suggests that these variant minibodies are better suited for use in therapeutic targeting and tumor imaging than existing anti-PSCA antibodies. Notably, tumor uptake in Capan-1 and HPAF-11 (data not shown) was roughly 2% and less than 1% in MIA PaCa-2 tumors, suggesting specific uptake.

RELATED ART

1) Sundaresan, G., Yazaki, P. J., Shively, J. E., Finn, R. D., Larson, S. M., Raubitschek, A. A., Williams, L. E., Chatzi-ioannou, A. F., Gambhir, S. S., and Wu, A. M. (2003) Iodine-124 labeled engineered anti-CEA minibodies and diabodies allow highcontrast, antigen-specific small-animal PET imaging of xenografts in athymic mice. J. Nucl. Med., 44:1962-1969.
2) Olafsen, T., Gu, Z., Sherman, M. A., Leyton, J. V., Witkosky, M. E., Shively, J. E., Raubitschek, A. A., Morrison, S. L., Wu, A. M. and Reiter, R. E. (2007) Targeting, imaging, and therapy using a humanized anti-prostate stem cell antigen (PSCA) antibody. J. Immunotherapy 30:396-405.
3) Leyton, Olafsen, T., Sherman, M. A., Reiter, R. E., and Wu, A. M. Anti-prostate stem cell antigen (PSCA) antibody fragments for PET imaging of prostate cancer (abstract). Cancer Biotherapy & Radiopharmaceuticals 21:391, 2006.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the extent consistent with the present disclosure.

What is claimed is:

1. An antigen binding protein construct that binds to human prostate stem cell antigen (PSCA) comprising an antigen binding domain comprising a heavy chain variable domain comprising the complementarity determining regions (CDRs) of the heavy chain variable domain of SEQ ID NO: 7 and a light chain variable domain comprising the CDRs of the light chain variable domain of SEQ ID NO: 7.

2. The antigen binding protein construct of claim 1, wherein said antigen binding domain comprises a light chain variable domain comprising the light chain variable domain of SEQ ID NO: 7.

3. The antigen binding protein construct of claim 1, wherein said antigen binding domain comprises a heavy chain variable domain comprising the heavy chain variable domain of SEQ ID NO: 7.

4. The antigen binding protein construct of claim 1, wherein the construct is a minibody.

5. The antigen binding protein construct of claim 4, wherein said minibody comprises an amino acid sequence that is at least 95% identical to SEQ ID NO: 12.

6. The antigen binding protein construct of claim 5, wherein said minibody comprises the amino acid sequence of SEQ ID NO: 12.

7. The antigen binding protein construct of claim 1, wherein the construct is a diabody.

8. The antigen binding protein construct of claim 1, wherein the construct is a humanized antibody.

9. The antigen binding protein construct of claim 1, wherein the construct is an affinity matured antibody.

10. The antigen binding protein construct of claim 1, wherein the construct is conjugated to a therapeutic agent.

11. The antigen binding protein construct of claim 10, wherein the therapeutic agent is a cytotoxic agent.

12. The antigen binding protein construct of claim 11, wherein the cytotoxic agent is selected from a group consisting of ricin, ricin A-chain, doxorubicin, daunotubicin, paclitaxel, ethiduim bromide, mitomycin, etoposide, tenoposide, vincristine, vinblastine, colchicine, dihydroxy anthracin dione, actinomycin D, diphteria toxin, Pseudomonas, exotoxin (PE) A, PE40, abrin, arbrin A chain, modeccin A chain, alpha-sarcin, gelonin mitogellin, retstrictocin, phenomycin, enomycin, curicin, crotin, calicheamicin, sapaonaria officinalis inhibitor, maytansinoids, and glucocorticoidricin.

13. The antigen binding protein construct of claim 10, wherein the therapeutic agent is a radioactive isotope.

14. The antigen binding protein construct of claim 13, wherein the radioactive isotope is $^{212}Bi$, $^{131}I$, $^{111}In$, $^{90}Y$ or $^{186}Re$.

15. The antigen binding protein construct of claim 1, wherein the construct is linked to an anti-cancer pro-drug activating enzyme capable of converting a pro-drug to its active form.

16. The antigen binding protein construct of claim 1, which is labeled with a detectable marker.

17. The antigen binding protein construct of claim 16, wherein the detectable marker is a radioisotope, a fluorescent compound, a bioluminescent compound, a chemiluminescent compound, a metal chelator or an enzyme.

18. The antigen binding protein construct of claim 16, wherein the detectable marker is $^{124}I$, $^{86}Y$, $^{18}F$, or $^{94}Tc$.

19. A pharmaceutical composition comprising the antigen binding protein construct of claim 1 and a pharmaceutically acceptable excipient, carrier, or stabilizer.

20. The composition of claim 19, which is formulated as an aqueous solution or a lyophilized solid.

21. A polynucleotide encoding the antigen binding protein construct of claim 1.

22. A method for inhibiting the growth of a prostate, pancreatic or bladder cancer cell expressing PSCA, said method comprising contacting said cancer cell with an antigen binding protein construct of claim 1, wherein said antigen binding protein construct is conjugated to an effector moiety that is effective to inhibit the growth of said cancer cell.

23. The method of claim 22, further comprising administering to the cancer cell a chemotherapeutic agent.

24. The method of claim 22, further comprising administering radiation therapy to the cancer cell.

25. A method for killing a prostate, pancreatic or bladder cancer cell expressing PSCA, said method comprising contacting said cancer cell with an antigen binding protein construct of claim 1, wherein said antigen binding protein construct is conjugated to an effector moiety that is effective to kill said cancer cell.

26. A method for treating a prostate, pancreatic or bladder cancer expressing PSCA in a patient, said method comprising administering to said patient an antigen binding protein construct of claim 1, wherein said antigen binding protein construct is conjugated to an effector moiety that is effective to inhibit the growth of said cancer.

27. The method of claim 26, further comprising administering to the patient hormone ablation therapy or hormone antagonist therapy.

28. The method of claim 26, wherein the antigen binding protein construct is administered intravenously, intraperitoneally, intramuscularly, intratumorally, or intradermally.

29. A method for imaging prostate, pancreatic or bladder cancer cells expressing PSCA in a patient, said method comprising administering to said patient an antigen binding protein construct of claim 1, wherein said antigen binding protein construct is conjugated to a detectable moiety, and detecting the presence and location of the antigen binding protein construct within the patient's body.

30. The method of claim 29, wherein imaging is performed using a method selected from the group consisting of magnetic resonance imaging (MRI), nuclear magnetic resonance (NMR), computerized axial tomography (CAT) scan, cooled charged coupled device (CCD) camera optical imaging, bioluminescent optical imaging, position emission tomography (PET), single photon emission computed tomography, and microPET.

31. A method for detecting a cancerous cell expressing PSCA, said method comprising contacting a sample comprising cells with an antigen binding protein construct of claim 1 and detecting any complex of a cancerous cell expressing PSCA and said antigen binding protein construct that forms.

32. An antibody that binds to human prostate stem cell antigen (PSCA) comprising an antigen binding domain comprising a heavy chain variable domain comprising the complementarity determining regions (CDRs) of the heavy chain variable domain of SEQ ID NO: 7 and a light chain variable domain comprising the CDRs of the light chain variable domain of SEQ ID NO: 7.

33. The antibody of claim 32, wherein said antibody is a minibody, a diabody, a scFv or a scFv-Fc.

* * * * *